(12) United States Patent
Lim et al.

(10) Patent No.: US 10,172,562 B2
(45) Date of Patent: Jan. 8, 2019

(54) MOBILE TERMINAL WITH HEALTH CARE FUNCTION AND METHOD OF CONTROLLING THE MOBILE TERMINAL

(71) Applicant: LG ELECTRONICS INC., Seoul (KR)

(72) Inventors: Gukchan Lim, Seoul (KR); Seonghyok Kim, Seoul (KR); Hyunghoon Oh, Seoul (KR); Jeunguk Ha, Seoul (KR); Seehyung Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 1264 days.

(21) Appl. No.: 13/799,102

(22) Filed: Mar. 13, 2013

(65) Prior Publication Data
US 2013/0310656 A1    Nov. 21, 2013

(30) Foreign Application Priority Data

May 21, 2012  (KR) .................. 10-2012-0053828
May 21, 2012  (KR) .................. 10-2012-0053829

(51) Int. Cl.
*A61B 5/00*  (2006.01)
*A61B 5/145*  (2006.01)
(Continued)

(52) U.S. Cl.
CPC .......... *A61B 5/6898* (2013.01); *A61B 5/0022* (2013.01); *A61B 5/0082* (2013.01);
(Continued)

(58) Field of Classification Search
CPC ... A61B 5/6898; A61B 5/0022; A61B 5/7282; A61B 5/742; A61B 5/746; A61B 5/7203;
(Continued)

(56) References Cited

U.S. PATENT DOCUMENTS

| | | | |
|---|---|---|---|
| 2004/0002637 A1* | 1/2004 | Huang | A61B 5/14551 600/300 |
| 2004/0117212 A1* | 6/2004 | Kong | G06Q 50/22 705/2 |

(Continued)

FOREIGN PATENT DOCUMENTS

| | | |
|---|---|---|
| KR | 10-2006-0003145 | 1/2006 |
| KR | 10-2008-0090194 | 10/2008 |
| KR | 10-2011-0057439 | 6/2011 |

*Primary Examiner* — Boniface Nganga
(74) *Attorney, Agent, or Firm* — KED & Associates, LLP

(57) ABSTRACT

The present invention relates to a mobile terminal with a health care function and a method of controlling the mobile terminal. An embodiment of the present invention relates to a mobile terminal with a health care function. The mobile terminal includes a sensing unit that senses a living body signal from a user and information on user's surroundings when performing the health care function, a controller that generates a numerically-valued living body information using the living body signal, sets a reference range of numerical values using the information on the user's surroundings and generates alerting information depending on whether or not a numerical value of the living body information falls into the reference range of numerical values, and a display unit that displays the alerting information under the control of the controller.

17 Claims, 19 Drawing Sheets

(51) Int. Cl.
  *A61B 5/0205*  (2006.01)
  *A61B 5/11*  (2006.01)
  *A61B 5/0402*  (2006.01)
  *G06F 19/00*  (2018.01)
  *G16H 40/67*  (2018.01)
  *A61B 5/024*  (2006.01)
  *A61B 5/0245*  (2006.01)
  *A61B 5/1455*  (2006.01)

(52) U.S. Cl.
  CPC .......... *A61B 5/0205* (2013.01); *A61B 5/0402* (2013.01); *A61B 5/14542* (2013.01); *A61B 5/7203* (2013.01); *A61B 5/7282* (2013.01); *A61B 5/742* (2013.01); *A61B 5/746* (2013.01); *G06F 19/00* (2013.01); *G16H 40/67* (2018.01); *A61B 5/0245* (2013.01); *A61B 5/02438* (2013.01); *A61B 5/1112* (2013.01); *A61B 5/14551* (2013.01); *A61B 5/6817* (2013.01); *A61B 5/721* (2013.01); *A61B 5/7275* (2013.01); *A61B 5/743* (2013.01); *A61B 2560/0242* (2013.01)

(58) Field of Classification Search
  CPC ... A61B 5/0402; A61B 5/0082; A61B 5/0205; A61B 5/14542; A61B 5/721; A61B 5/743; A61B 5/02438; A61B 5/0245; A61B 5/14551; A61B 5/6817; A61B 5/7275; A61B 5/1112; A61B 2560/0242; G16H 40/67

See application file for complete search history.

(56) References Cited

U.S. PATENT DOCUMENTS

| | | | |
|---|---|---|---|
| 2004/0133081 A1* | 7/2004 | Teller | A61B 5/01 600/300 |
| 2006/0206010 A1* | 9/2006 | Iida | A61B 5/0002 600/300 |
| 2007/0197881 A1* | 8/2007 | Wolf | A61B 5/0002 600/300 |
| 2008/0162182 A1* | 7/2008 | Cazares | G06Q 50/22 705/2 |
| 2008/0249382 A1 | 10/2008 | Oh et al. | |
| 2009/0112114 A1* | 4/2009 | Ayyagari | A61B 5/08 600/529 |
| 2009/0131759 A1* | 5/2009 | Sims | A61B 5/1135 600/301 |
| 2010/0063365 A1* | 3/2010 | Pisani | A61B 5/0002 600/301 |
| 2010/0217099 A1* | 8/2010 | LeBoeuf | A61B 5/00 600/301 |
| 2010/0217100 A1* | 8/2010 | LeBoeuf | A61B 5/00 600/301 |

* cited by examiner

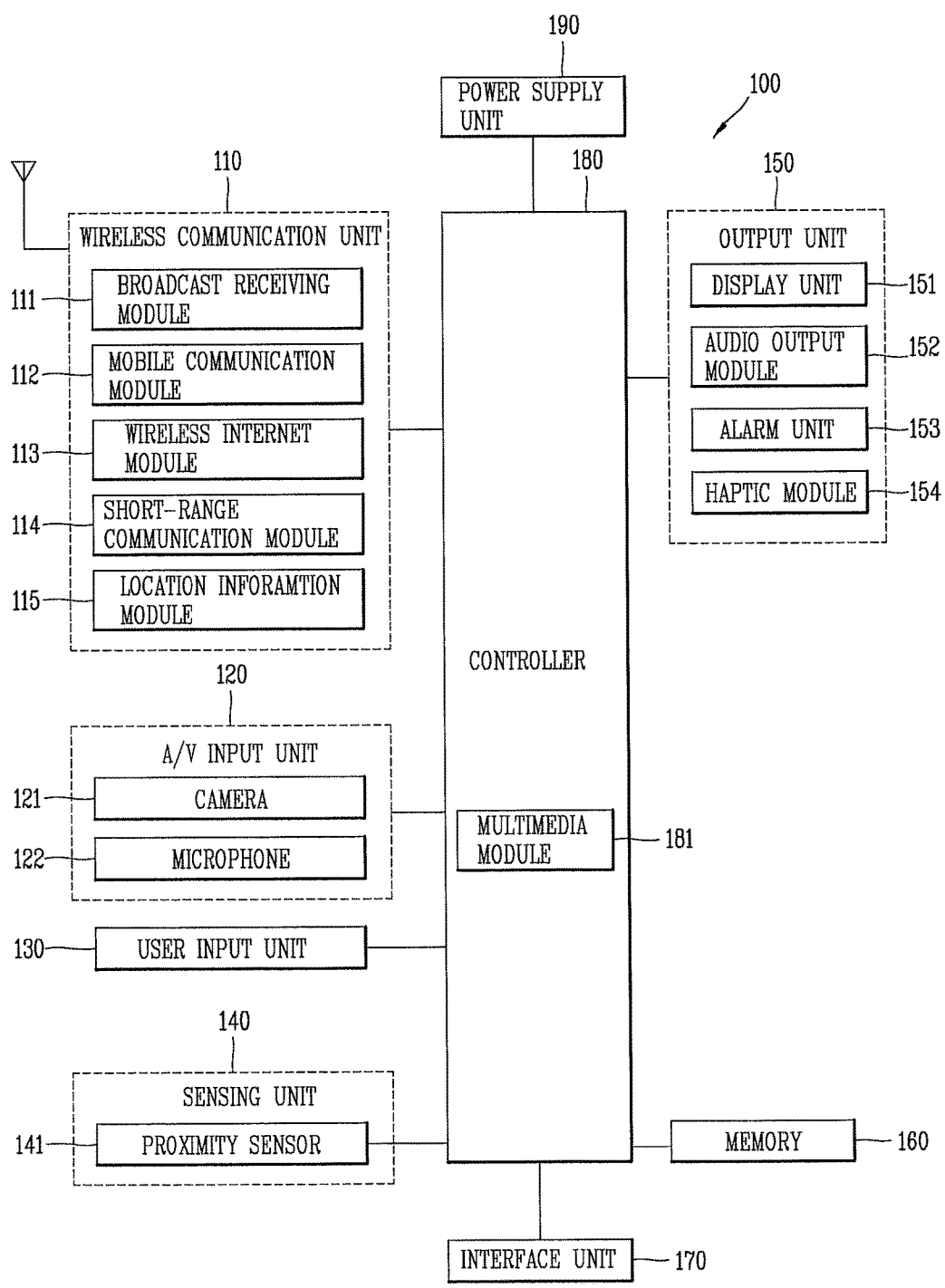

FIG. 6A

| PRESSURE(atm) | TEMPERATURE(°C) | HUMIDITY(%) | REFERENCE RANGE OF VALUES FOR NUMBER OF HEARTBEATS(TIMES PER ONE MINUTE) |
|---|---|---|---|
| 1.00 | 15 or 28 | 40 or 80 | FROM 61 TO 79 |
| 0.98 | 14 or 29 | 36 or 84 | FROM 62 TO 78 |
| 0.96 | 13 or 30 | 32 or 88 | FROM 63 TO 77 |
| 0.94 | 12 or 31 | 28 or 92 | FROM 64 TO 76 |
| 0.92 | 11 or 32 | 24 or 96 | FROM 65 TO 75 |

FIG. 6B

| PRESSURE(atm) | TEMPERATURE(°C) | HUMIDITY(%) | REFERNCE RANGE OF VALUES FOR SATURATION OF OXYGEN IN BLOOD(%) |
|---|---|---|---|
| 1.00 | 15 or 28 | 40 or 80 | 97.0 OR MORE |
| 0.98 | 14 or 29 | 36 or 84 | 97.3 OR MORE |
| 0.96 | 13 or 30 | 32 or 88 | 97.6 OR MORE |
| 0.94 | 12 or 31 | 28 or 92 | 97.9 OR MORE |
| 0.92 | 11 or 32 | 24 or 96 | 98.2 OR MORE |

- S410 — CONFIRM INFORMATION ON USER'S PERSONAL CHARACTERISTICS
- S420 — DETERMINE AMOUNT OF ELCTRIC CURRENT DRIVING LIGHT EMITTING UNIT BASED ON USER'S PERSONAL CHARACTERISTICS

| SKIN THICKNESS(mm) | AMOUNT OF ELCTRIC CURRENT DRIVING LIGHT EMITTING UNIT(mA) |
|---|---|
| 0.5 | 3 |
| 0.6 | 4 |
| 0.7 | 5 |
| 0.8 | 6 |

| MEASURED SNR | REFERNCE IN VALUE | DIFFERENCE IN VALUE | INCREASING AMOUNT OF ELECTRIC CURRENT DRIVING LIGHT EMITTING UNIT(mA) |
|---|---|---|---|
| 60 | | +5 | 0 |
| 55 | | 0 | 0 |
| 50 | 55 | −5 | 2 |
| 45 | | −10 | 4 |
| 40 | | −15 | 6 |
| 35 | | −20 | 8 |

FIG. 10A

S610 — DETECT MOTION OF MAIN BODY

S620 — DETERMINE AMOUNT OF ELECTRIC CURRENT DRIVING LIGHT EMITTING UNIT BASED ON MOTION OF MAIN BODY

FIG. 10B

| DEGREE OF MOTION(G) | AMOUNT OF ELECTRIC CURRENT DRIVING LIGHT EMITTING UNIT(mA) |
|---|---|
| 0.2 | 2 |
| 0.4 | 4 |
| 0.6 | 6 |
| 0.8 | 8 |
| 1.0 | 10 |

MOBILE TERMINAL WITH HEALTH CARE FUNCTION AND METHOD OF CONTROLLING THE MOBILE TERMINAL

CROSS-REFERENCE TO RELATED APPLICATION

Pursuant to 35 U.S.C. § 119(a), this application claims the benefit of earlier filing date and right of priority to Korean Applications No. 10-2012-0053828 and No. 10-2012-0053829, both filed on May 21, 2012, the contents of which is incorporated by reference herein in its entirety.

BACKGROUND OF THE INVENTION

1. Field of the Invention

The present invention relates to a mobile terminal and more particularly to a mobile terminal with a function of sensing a living body signal and a health care function, and a method of controlling the mobile terminal.

2. Description of the Conventional Art

Terminals can be divided into mobile/portable terminals and stationary terminals according to their mobility. The portable terminals can be divided into handheld terminals and vehicle mount terminals according to whether a user directly carries his or her terminal.

As such a mobile terminal becomes multifunctional, the mobile terminal can be allowed to capture still images or moving images, play music or video files, play games, receive broadcast, etc., so as to be implemented as an integrated multimedia player. In order to support and enhance such functions of the terminal, it can be considered to improve configuration and/or software of the terminal.

With the help of these improvements, a health care function is provided that is able to be performed in the mobile terminal. The user may check and manage his/her health state through the use of the health care function. However, user's surroundings need to be taken into consideration as a critical factor in correctly checking his/her health state and providing him/her with feedback on his/her health state. In addition, the health care function entails an operation of sensing a user's living body signal, and his/her health state is based on a result of analyzing his/her living body signal. Accordingly, reliability of the living body signal needs to be secured to correctly manage the user's health state.

SUMMARY OF THE INVENTION

Therefore, an aspect of the detailed description is to provide a mobile terminal with a health care function that is adaptable to user's surroundings.

Another object of the detailed description is to provide a mobile terminal that is capable of alerting a user to an expected degree of a hazard associated with a user's health state in advance on the basis of a district.

A further object of the detailed description is to improve reliability of a living body signal that is sensed in a mobile terminal with a health care function.

To achieve these and other advantages and in accordance with the purpose of this specification, as embodied and broadly described herein, there is provided a mobile terminal with a health care function, including a sensing unit that senses a living body signal from a user and information on user's surroundings when performing the health care function, a controller that generates a numerically-valued living body information using the living body signal, sets a reference range of numerical values using the information on the user's surroundings and generates alerting information depending on whether or not a numerical value of the living body information falls into the reference range of numerical values, and a display unit that displays the alerting information under the control of the controller.

The mobile terminal with a health care function may further include a location information module that obtains information on location of the mobile terminal, and a database that stores the location information and the living body information, the surroundings information, and the alerting information in association with one another.

In the mobile terminal with a health care function, the controller may generate map information representing an expected degree of a hazard on the basis of a district using statistical data relating to the information stored in the database.

In the mobile terminal with a health care function, the controller may update the map information in a case where a change occurs in at least part of the statistical data.

In the mobile terminal with a health care function, the controller may determine an alerting level of the alerting information, based on the degree to which the numerical value of the living body signal is out of the reference range of the numerical values.

In the mobile terminal with a health care function, the sensing unit may respond to a change in location of the mobile terminal to sense the living body signal and the surroundings information.

In the mobile terminal with a health care function, the living body signal may include at least one of an electrocardiogram (ECG) signal, and a photoplethysmography (PPG) signal.

In the mobile terminal with a health care function, the living body information may include at least one of the number of heartbeats and oxygen saturation in blood.

In the mobile terminal with a health care function, the surroundings information may include at least one of pressure information, temperature information, and humidity information.

To achieve these and other advantages and in accordance with the purpose of this specification, as embodied and broadly described herein, there is provided a method of controlling a mobile terminal with a health care function, including sensing a living body signal from a user and information on user's surroundings information when performing the health care function, generating numerically-valued living body information using the living body signal, setting a reference range of numerical values using the information on the user's surroundings, generating alerting information depending on whether or not a numerical value of the living body information falls into the reference range of numerical values and displaying the alerting information.

The method of controlling a mobile terminal with a health care function may further include obtaining information on location of the mobile terminal and storing the location information and the living body information, the surroundings information, and the alerting information in a database, in association with one another. The method of controlling a mobile terminal with a health care function may further include generating map information representing an expected degree of a hazard on the basis of a district using statistical data relating to the information stored in the database. The method of controlling a mobile terminal with a health care function may further include updating the map information in a case where a change occurs in at least part of the statistical data.

In the generating of the alerting information in the method of controlling a mobile terminal with a health care function, an alerting level of the alerting information may be determined, based on the degree to which the numerical value of the living body signal is out of the reference range of the numerical values. In the method of controlling a mobile terminal with a health care function, in the sensing of the living body signal and the surroundings information, the living body signal and the surroundings information may be sensed by responding to a change in location of the mobile terminal.

To achieve these and other advantages and in accordance with the purpose of this specification, as embodied and broadly described herein, there is provided a mobile terminal with a health care function, including a living body sensing module which includes a light emitting unit which emits incident light to an object, and a light receiving unit which receives reflection light reflected the object, and that senses a living body signal using the reflection light, a measurement unit that measures a signal to noise ratio (SNR) of the living body signal, and a controller that controls electric current driving the light emitting unit in such a manner that strength of the incident light is adjusted depending on a result of comparing a reference value with the measured signal to noise ratio.

In the mobile terminal with a health care function, the controller may increase an amount of the electric current driving the light emitting unit, when the measured signal to noise ratio is smaller than the reference value as the result of the comparison. In the mobile terminal with a health care function, the controller may determine the amount of the electric current driving the light emitting unit, based on information on user's personal characteristics. In the mobile terminal with a health care function, the controller may compute a difference in value between the measured signal to noise ratio and the reference value and may determine the amount of the electric current driving the light emitting unit, based on the difference in value.

The mobile terminal with a health care function may further include a detection unit that detects a motion of the main body of the mobile terminal. In the mobile terminal with a health care function, the controller may determine the amount of the electric current driving the light emitting unit, based on the motion of the main body of the mobile terminal.

In the mobile terminal with a health care function, the controller may generate information on the user's health state by analyzing the living body signal. The mobile terminal with a health care function may further include a display unit that displays a result of analyzing the living body signal and the information on the user's health state.

In the mobile terminal with a health care function, the living body signal sensing module may be positioned in the main body of the mobile terminal or an accessory device that connects to the main body of the mobile terminal.

In the mobile terminal with a health care function, the living body signal may include a photoplethysmograph (PPG) signal.

To achieve these and other advantages and in accordance with the purpose of this specification, as embodied and broadly described herein, there is provided a method of controlling a mobile terminal with a health care function, including emitting incident light generated by a light emitting unit to an object, sensing a living body signal from the object using reflection light reflected in the object, measuring a signal to noise ratio of the living body signal, and controlling electric current driving the light emitting unit in such a manner that strength of the incident light is adjusted depending on a result of comparing a reference value with the measured signal to noise ratio.

In the method of controlling a mobile terminal with a health care function, the controlling of the electric current driving the light emitting unit may include increasing an amount of the electric current driving the light emitting unit when the measured signal to noise ratio is smaller than the reference value as the result of the comparison.

In the emitting of the incident light to the object, or in the controlling of the electric current driving the light emitting unit, in the method of controlling a mobile terminal with a health care function, the amount of the electric current driving the light emitting unit may be determined based on information on user's personal characteristics.

In the controlling of the electric current driving the light emitting unit, in the method of controlling a mobile terminal with a health care function, the electric current driving the light emitting unit may be determined based on a difference in value between the measured signal to noise ratio and the reference value.

The method of controlling a mobile terminal with a health care function may further include detecting a motion of the main body of the mobile terminal. In the emitting of the incident light to the object, or in the controlling of the electric current driving the light emitting unit, in the method of controlling a mobile terminal with a health care function, the amount of the electric current driving the light emitting unit may be determined based on the motion of the main body of the mobile terminal.

The method of controlling a mobile terminal with a health care function may further include generating information on a user's health state by analyzing the living body signal, and displaying a result of analyzing the living body signal and the information on the user's health state.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings:

FIG. 1 is a block diagram illustrating a mobile terminal according to the present invention;

FIGS. 6A and 6B are views, each illustrating a data table stored in a database according to the embodiment of the present invention;

FIG. 10A is a flow chart for describing the embodiment of the method of controlling the electric current driving the light emitting unit;

FIG. 10B is a view illustrating the data table referred to in the control method of controlling the electric current driving the light emitting unit as illustrated FIG. 10A;

DETAILED DESCRIPTION OF THE INVENTION

Figure 2A:
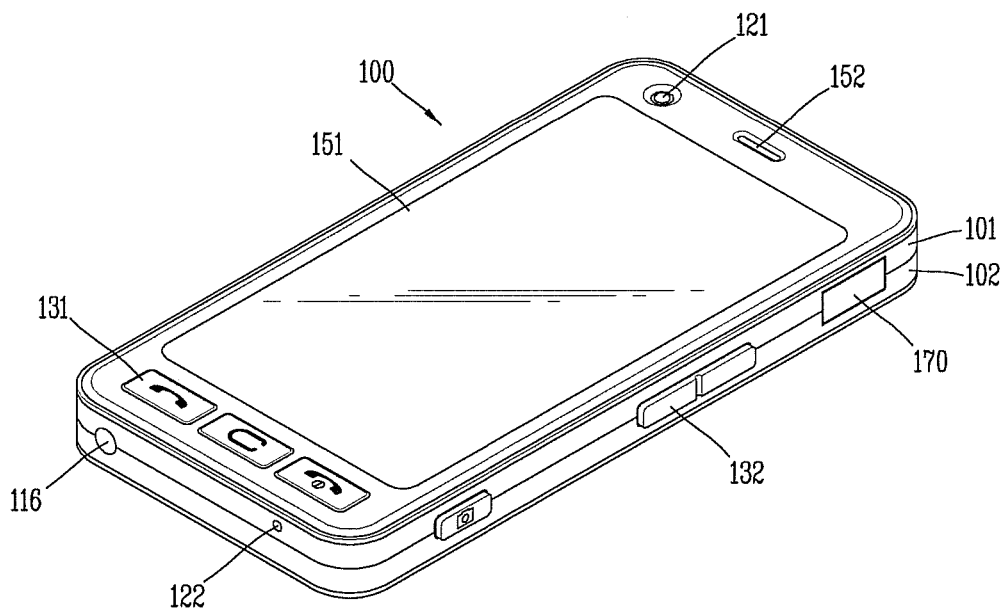
FIGS. 2A and 2B are perspective views, each illustrating an external appearance of the mobile terminal according to the present invention.

Description will now be given in detail of the exemplary embodiments, with reference to the accompanying drawings. For the sake of brief description with reference to the drawings, the same or equivalent components will be provided with the same reference numbers, and description thereof will not be repeated.

A mobile terminal according to the present disclosure may include a portable phone, a smart phone, a laptop computer, a digital broadcasting terminal, Personal Digital Assistants (PDA), Portable Multimedia Player (PMP), a navigation system, etc. However, it will be obvious to those skilled in the art that the present invention may be also applicable to a fixed terminal such as a digital TV and a desktop computer.

FIG. 1 is a block diagram of a mobile terminal 100 according to the present invention. Referring to FIG. 1, the mobile terminal 100 includes a wireless communication unit 110, an A/V (Audio/Video) input unit 120, a user input unit 130, a sensing unit 140, an output unit 150, a memory 160, an interface unit 170, a controller 180, and a power supply unit 190. FIG. 1 shows the mobile terminal 100 having various components, but it is understood that implementing all of the illustrated components is not a requirement. The mobile terminal 100 may be implemented by greater or fewer components.

Hereinafter, each of the above components 110-190 of the mobile terminal 100 will be explained.

The wireless communication unit 110 typically includes one or more components allowing radio communication between the mobile terminal 100 and a wireless communication system or a network in which the mobile terminal is located. For example, the wireless communication unit 110 may include at least one of a broadcast receiving module 111, a mobile communication module 112, a wireless Internet module 113, a short-range communication module 114, and a location information module 115.

The broadcast receiving module 111 receives broadcast signals and/or broadcast associated information from an external broadcast management server (or other network entity) via a broadcast channel. The broadcast associated information may refer to information associated with a broadcast channel, a broadcast program or a broadcast service provider. The broadcast associated information may be provided via a mobile communication network. In this case, the broadcast associated information may be received by the mobile communication module 112. Broadcasting signals and/or broadcasting associated information received through the broadcast receiving module 111 may be stored in the memory 160.

The mobile communication module 112 transmits/receives wireless signals to/from at least one of network entities (e.g., base station, an external terminal, a server, etc.) on a mobile communication network. Here, the wireless signals may include audio call signal, video call signal, or various formats of data according to transmission/reception of text/multimedia messages.

The wireless internet module 113 supports wireless Internet access for the mobile terminal. This module may be internally or externally coupled to the mobile terminal 100. Examples of such wireless Internet access may include Wireless LAN (WLAN) (Wi-Fi), Wireless Broadband (Wibro), World Interoperability for Microwave Access (Wimax), High Speed Downlink Packet Access (HSDPA), and the like.

The short-range communication module 114 denotes a module for short-range communications. Suitable technologies for implementing this module may include BLUETOOTH, Radio Frequency IDentification (RFID), Infrared Data Association (IrDA), Ultra-WideBand (UWB), ZigBee, and the like.

The position information module 115 denotes a module for sensing or calculating a position of a mobile terminal. An example of the position information module 115 may include a Global Position System (GPS) module.

Referring to FIG. 1, the A/V input unit 120 is configured to receive an audio or video signal. The A/V input unit 120 may include a camera 121, a microphone 122 or the like. The camera 121 processes image data of still pictures or video acquired by an image capture device in a video capturing mode or an image capturing mode. The processed image frames may be displayed on a display unit 151. The image frames processed by the camera 121 may be stored in the memory 160 or transmitted via the wireless communication unit 110. The camera 121 may be provided in two or more according to the configuration of the mobile terminal.

The microphone 122 may receive sounds (audible data) via a microphone in a phone call mode, a recording mode, a voice recognition mode, and the like, and can process such sounds into audio data. The processed audio (voice) data may be converted for output into a format transmittable to a mobile communication base station via the mobile communication module 112 in case of the phone call mode. The microphone 122 may implement various types of noise canceling (or suppression) algorithms to cancel (or suppress) noise or interference generated in the course of receiving and transmitting audio signals.

The user input unit 130 may generate key input data from commands entered by a user to control various operations of the mobile communication terminal. The user input unit 130 may include a keypad, a dome switch, a touch pad (e.g., a touch sensitive member that detects changes in resistance, pressure, capacitance, etc. due to being contacted) a jog wheel, a jog switch, and the like.

The sensing unit 140 detects a current status (or state) of the mobile terminal 100 such as an opened or closed state of the mobile terminal 100, a location of the mobile terminal 100, the presence or absence of user contact with the mobile terminal 100, the orientation of the mobile terminal 100, an acceleration or deceleration movement and direction of the mobile terminal 100, etc., and generates commands or signals for controlling the operation of the mobile terminal 100. For example, when the mobile terminal 100 is implemented as a slide type mobile phone, the sensing unit 140 may sense whether the slide phone is open or closed. In addition, the sensing unit 140 can detect whether or not the power supply unit 190 supplies power or whether or not the interface unit 170 is coupled with an external device.

The sensing unit 140 may include a proximity sensor 141. Further, the sensing unit 140 may include a touch sensor (not shown) for sensing a touch operation with respect to the display unit 151.

The touch sensor may be implemented as a touch film, a touch sheet, a touch pad, and the like. The touch sensor may be configured to convert changes of a pressure applied to a specific part of the display unit 151, or a capacitance occurring from a specific part of the display unit 151, into electric input signals. Also, the touch sensor may be configured to sense not only a touched position and a touched area, but also a touch pressure.

Here, if the touch sensor and the display unit 151 have a layered structure therebetween, the display unit 151 may be used as an input device rather than an output device. The display unit 151 may be referred to as a touch screen.

When touch inputs are sensed by the touch sensors, corresponding signals are transmitted to a touch controller (not shown). The touch controller processes the received signals, and then transmits corresponding data to the controller 180. Accordingly, the controller 180 may sense which region of the display unit 151 has been touched.

When the touch screen is implemented as a capacitance type, proximity of a pointer to the touch screen is sensed by changes of an electromagnetic field. In this case, the touch screen (touch sensor) may be categorized into a proximity sensor 141.

The proximity sensor 141 indicates a sensor to sense presence or absence of an object approaching to a surface to be sensed, or an object disposed near a surface to be sensed, by using an electromagnetic field or infrared rays without a mechanical contact. The proximity sensor 141 has a longer lifespan and a more enhanced utility than a contact sensor. The proximity sensor 141 may include a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and so on.

In the following description, for the sake of brevity, recognition of the pointer positioned to be close to the touch screen without being contacted will be called a 'proximity touch', while recognition of actual contacting of the pointer on the touch screen will be called a 'contact touch'. In this case, when the pointer is in the state of the proximity touch, it means that the pointer is positioned to correspond vertically to the touch screen.

The proximity sensor detects a proximity touch and a proximity touch pattern (e.g., a proximity touch distance, a proximity touch speed, a proximity touch time, a proximity touch position, a proximity touch movement state, or the like), and information corresponding to the detected proximity touch operation and the proximity touch pattern can be outputted to the touch screen.

The output unit 150 is configured to provide outputs in a visual, audible, and/or tactile manner (e.g., audio signal, video signal, alarm signal, vibration signal, etc.). The output unit 150 may include the display unit 151, an audio output module 152, an alarm unit 153, a haptic module 154, and the like.

The display unit 151 may display information processed in the mobile terminal 100. For example, when the mobile terminal 100 is in a phone call mode, the display unit 151 may display a User Interface (UI) or a Graphic User Interface (GUI) associated with a call or other communication (such as text messaging, multimedia file downloading, etc.). When the mobile terminal 100 is in a video call mode or image capturing mode, the display unit 151 may display a captured image and/or received image, a UI or GUI.

The display unit 151 may include at least one of a Liquid Crystal Display (LCD), a Thin Film Transistor-LCD (TFT-LCD), an Organic Light Emitting Diode (OLED) display, a flexible display, a three-dimensional (3D) display, or the like.

Some of these displays may be configured to be transparent so that outside may be seen therethrough, which may be referred to as a transparent display. A representative example of the transparent display may include a Transparent Organic Light Emitting Diode (TOLED), and the like. That is, the display unit 151 may include a first surface and a second surface overlapping each other, and the first and second surfaces may be formed to be transparent or light-transmissive. Under such configuration, a user can view an object positioned at a rear side of a body through a region occupied by the display unit 151 of the body. Such display unit 151 may be referred to as a transparent display 155.

The display unit 151 may be implemented in two or more in number according to a configured aspect of the mobile terminal 100. For instance, a plurality of displays may be arranged on one surface integrally or separately, or may be arranged on different surfaces.

The audio output module 152 may convert and output as sound audio data received from the wireless communication unit 110 or stored in the memory 160 in a call signal reception mode, a call mode, a record mode, a voice recognition mode, a broadcast reception mode, and the like. Also, the audio output module 152 may provide audible outputs related to a particular function performed by the mobile terminal 100 (e.g., a call signal reception sound, a message reception sound, etc.). The audio output module 152 may include a speaker, a buzzer, and so on.

The alarm unit 153 may provide outputs to inform about the occurrence of an event of the mobile terminal 100. Typical events may include call reception, message reception, key signal inputs, a touch input, etc. In addition to audio or video outputs, the alarm unit 153 may provide outputs in a different manner to inform about the occurrence of an event. The video signal or the audio signal may be output via the display unit 151 or the audio output module 152. Accordingly, the display unit 151 or the audio output module 152 may be classified as part of the alarm unit 153.

The haptic module 154 generates various tactile effects which a user can feel. A representative example of the tactile effects generated by the haptic module 154 includes vibration. Vibration generated by the haptic module 154 may have a controllable intensity, a controllable pattern, and so on. For instance, different vibration may be output in a synthesized manner or in a sequential manner.

The haptic module 154 may generate various tactile effects, including not only vibration, but also arrangement of pins vertically moving with respect to a skin being touched (contacted), air injection force or air suction force through an injection hole or a suction hole, touch by a skin surface, presence or absence of contact with an electrode, effects by stimulus such as an electrostatic force, reproduction of cold or hot feeling using a heat absorbing device or a heat emitting device, and the like.

The haptic module 154 may be configured to transmit tactile effects (signals) through a user's direct contact, or a user's muscular sense using a finger or a hand. The haptic module 154 may be implemented in two or more in number according to the configuration of the mobile terminal 100.

The memory 160 may store a program for the processing and control of the controller 180. Alternatively, the memory 160 may temporarily store input/output data (e.g., phonebook data, messages, still images, video and the like). Also, the memory 160 may store data relating to various patterns of vibrations and audio output upon the touch input on the touch screen.

The memory 160 may be implemented using any type of suitable storage medium including a flash memory type, a hard disk type, a multimedia card micro type, a memory card type (e.g., SD or DX memory), Random Access Memory (RAM), Static Random Access Memory (SRAM), Read-Only Memory (ROM), Electrically Erasable Programmable Read-only Memory (EEPROM), Programmable Read-only Memory (PROM), magnetic memory, magnetic disk, optical disk, and the like. Also, the mobile terminal 100 may operate a web storage which performs the storage function of the memory 160 on the Internet.

The interface unit 170 may generally be implemented to interface the mobile terminal with external devices. The interface unit 170 may allow a data reception from an external device, a power delivery to each component in the mobile terminal 100, or a data transmission from the mobile terminal 100 to an external device. The interface unit 170 may include, for example, wired/wireless headset ports, external charger ports, wired/wireless data ports, memory card ports, ports for coupling devices having an identification module, audio Input/Output (I/O) ports, video I/O ports, earphone ports, and the like.

The identification module may be configured as a chip for storing various information required to authenticate an authority to use the mobile terminal 100, which may include a User Identity Module (UIM), a Subscriber Identity Module (SIM), a Universal Subscriber Identity Module (USIM), and the like. Also, the device having the identification module (hereinafter, referred to as 'identification device') may be implemented in a type of smart card. Hence, the identification device can be coupled to the mobile terminal 100 via a port.

Also, the interface unit 170 may serve as a path for power to be supplied from an external cradle to the mobile terminal 100 when the mobile terminal 100 is connected to the external cradle or as a path for transferring various command signals inputted from the cradle by a user to the mobile terminal 100. Such various command signals or power inputted from the cradle may operate as signals for recognizing that the mobile terminal 100 has accurately been mounted to the cradle.

The controller 180 typically controls the overall operations of the mobile terminal 100. For example, the controller 180 performs the control and processing associated with telephony calls, data communications, video calls, and the like. The controller 180 may include a multimedia module 181 which provides multimedia playback. The multimedia module 181 may be configured as part of the controller 180 or as a separate component. The controller 180 can perform a pattern recognition processing so as to recognize writing or drawing input on the touch screen as text or image.

The power supply unit 190 receives external power or internal power and supplies appropriate power required for operating respective elements and components under the control of the controller 180.

Various embodiments described herein may be implemented in a computer-readable or its similar medium using, for example, software, hardware, or any combination thereof.

For hardware implementation, the embodiments described herein may be implemented by using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic units designed to perform the functions described herein. In some cases, such embodiments may be implemented by the controller 180 itself.

For software implementation, the embodiments such as procedures or functions described herein may be implemented by separate software modules. Each software module may perform one or more functions or operations described herein. Software codes can be implemented by a software application written in any suitable programming language. The software codes may be stored in the memory 160 and executed by the controller 180.

Hereinafter, will be explained a method for processing a user's input to the mobile terminal 100.

The user input unit 130 is manipulated to receive a command for controlling the operation of the mobile terminal 100, and may include a plurality of manipulation units. The manipulation units may be referred to as manipulating portions, and may include any type of ones that can be manipulated in a user's tactile manner.

Various types of visible information may be displayed on the display unit 151. Such information may be displayed in several forms, such as character, number, symbol, graphic, icon or the like. Alternatively, such information may be implemented as a 3D stereoscopic image. For input of the information, at least one of characters, numbers, graphics or icons may be arranged and displayed in a preset configuration, thus being implemented in the form of a keypad. Such keypad may be called 'soft key.'

The display unit 151 may be operated as a single entire region or by being divided into a plurality of regions. For the latter, the plurality of regions may cooperate with one another. For example, an output window and an input window may be displayed at upper and lower portions of the display unit 151, respectively. Soft keys representing numbers for inputting telephone numbers or the like may be output on the input window. When a soft key is touched, a number or the like corresponding to the touched soft key is output on the output window. Upon manipulating the manipulation unit, a call connection for a telephone number displayed on the output window is attempted, or a text output on the output window may be input to an application.

In addition to the input manner illustrated in the embodiments, the display unit 151 or the touch pad may be scrolled to receive a touch input. A user may scroll the display unit 151 or the touch pad to move a cursor or pointer positioned on an object (subject), e.g., an icon or the like, displayed on the display unit 151. In addition, in case of moving a finger on the display unit 151 or the touch pad, the path of the finger being moved may be visibly displayed on the display unit 151, which can be useful upon editing an image displayed on the display unit 151.

One function of the mobile terminal may be executed in correspondence with a case where the display unit 151 (touch screen) and the touch pad are touched together within a preset time. An example of being touched together may include clamping a body with the user's thumb and index fingers. The one function, for example, may be activating or deactivating of the display unit 151 or the touch pad.

Figure 2B:
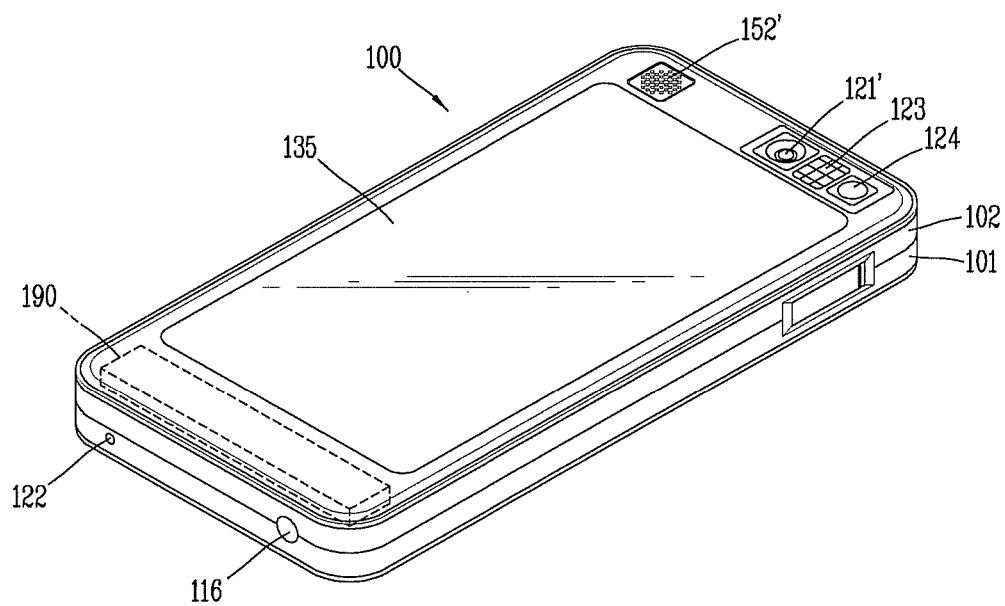

FIGS. 2A and 2B are perspective views showing the appearance of the mobile terminal 100 according to the present invention. FIG. 2A is a view showing a front surface and one side surface of the mobile terminal 100 in accordance with the present invention, and FIG. 2B is a view showing a rear surface and another side surface of the mobile terminal 100 of FIG. 2A.

As shown in FIG. 2A, the mobile terminal 100 is a bar type mobile terminal. However, the present invention is not limited to this, but may be applied to a slide type in which two or more bodies are coupled to each other so as to perform a relative motion, a folder type, or a swing type, a swivel type and the like.

A case (casing, housing, cover, etc.) forming an outer appearance of a body may include a front case 101 and a rear case 102. A space formed by the front case 101 and the rear case 102 may accommodate various components therein. At least one intermediate case may further be disposed between the front case 101 and the rear case 102.

Such cases may be formed by injection-molded synthetic resin, or may be formed using a metallic material such as stainless steel (STS) or titanium (Ti).

At the front case 101, may be disposed a display unit 151, an audio output unit 152, a camera 121, a user input unit 130 (refer to FIG. 1), a microphone 122, an interface unit 170, etc.

The display unit 151 occupies most parts of a main surface of the front case 101. The audio output unit 152 and the camera 121 are arranged at a region adjacent to one end of the display unit 151, and the user input unit 131 and the microphone 122 are arranged at a region adjacent to another end of the display unit 151. The user input unit 132, the interface unit 170, etc. may be arranged on side surfaces of the front case 101 and the rear case 102.

The user input unit 130 is manipulated to receive a command for controlling the operation of the mobile terminal 100, and may include a plurality of manipulation units 131 and 132.

The manipulation units 131 and 132 may receive various commands. For instance, the first manipulation 131 is configured to input commands such as START, END, SCROLL or the like, and the second manipulation unit 132 is configured to input commands for controlling a level of sound outputted from the audio output unit 152, or commands for converting the current mode of the display unit 151 to a touch recognition mode.

Referring to FIG. 2B, a camera 121' may be additionally provided on the rear case 102. The camera 121' faces a direction which is opposite to a direction faced by the camera 121 (refer to FIG. 2A), and may have different pixels from those of the camera 121.

For example, the camera 121 may operate with relatively lower pixels (lower resolution). Thus, the camera 121 may be useful when a user can capture his face and send it to another party during a video call or the like. On the other hand, the camera 121' may operate with a relatively higher pixels (higher resolution) such that it can be useful for a user to obtain higher quality pictures for later use. The cameras 121 and 121' may be installed at the terminal body so as to rotate or pop-up.

A flash 123 and a mirror 124 (not shown) may be additionally disposed close to the camera 121'. The flash 123 operates in conjunction with the camera 121' when taking a picture using the camera 121'. The mirror 124 can cooperate with the camera 121' to allow a user to photograph himself in a self-portrait mode.

An audio output unit 152' may be additionally arranged on a rear surface of the terminal body. The audio output unit 152' may cooperate with the audio output unit 152 (refer to FIG. 2A) disposed on a front surface of the terminal body so as to implement a stereo function. Also, the audio output unit 152' may be configured to operate as a speakerphone.

A broadcast signal receiving antenna 116 as well as an antenna for calling may be additionally disposed on a side surface of the terminal body. The broadcast signal receiving antenna 116 of the broadcast receiving module 111 (refer to FIG. 1) may be configured to retract into the terminal body.

A power supply unit 190 for supplying power to the mobile terminal 100 is mounted to the body. The power supply unit 190 may be mounted in the body, or may be detachably mounted to the body.

A touch pad 135 for sensing touch may be additionally mounted to the rear case 102. Like the display unit 151 (refer to FIG. 2A), the touch pad 135 may be formed to be light-transmissive. The touch pad 135 may be also additionally mounted with a rear display unit for outputting visual information. Information output from the display unit 151 (front display) and the rear display can be controlled by the touch pad 135.

The touch pad 135 operates in association with the display unit 151. The touch pad 135 may be disposed on the rear surface of the display unit 151 in parallel. The touch pad 135 may have a size equal to or smaller than that of the display unit 151.

The mobile terminal is described below which senses a living body signal and information on user's surroundings and performs a health care function using this information. The living body signal according to an embodiment of the present invention may include an electrocardiogram (ECG) signal (hereinafter referred to as an "ECG signal"), a photoplethysmo-graphy (PPG) signal (hereinafter referred to as a 'PPG signal') and the like. Here the ECG signal is a signal that represents active electric current occurring in heart muscle during heartbeat. More particularly, the ECG signal is sensed by electrodes attached to the outer surface of skin and recorded by an ammeter. Then, the PPG is a living body signal that represents the degree to which blood vessels contract and expand. More particularly, when a near-infra-red-ray optical signal is emitted to the outer surface of the skin, the PPG represents a change in an amount of blood that is obtained by analyzing light penetrating hemoglobin without being absorbed by the hemoglobin or by analyzing light being reflected in the hemoglobin.

Figure 3:
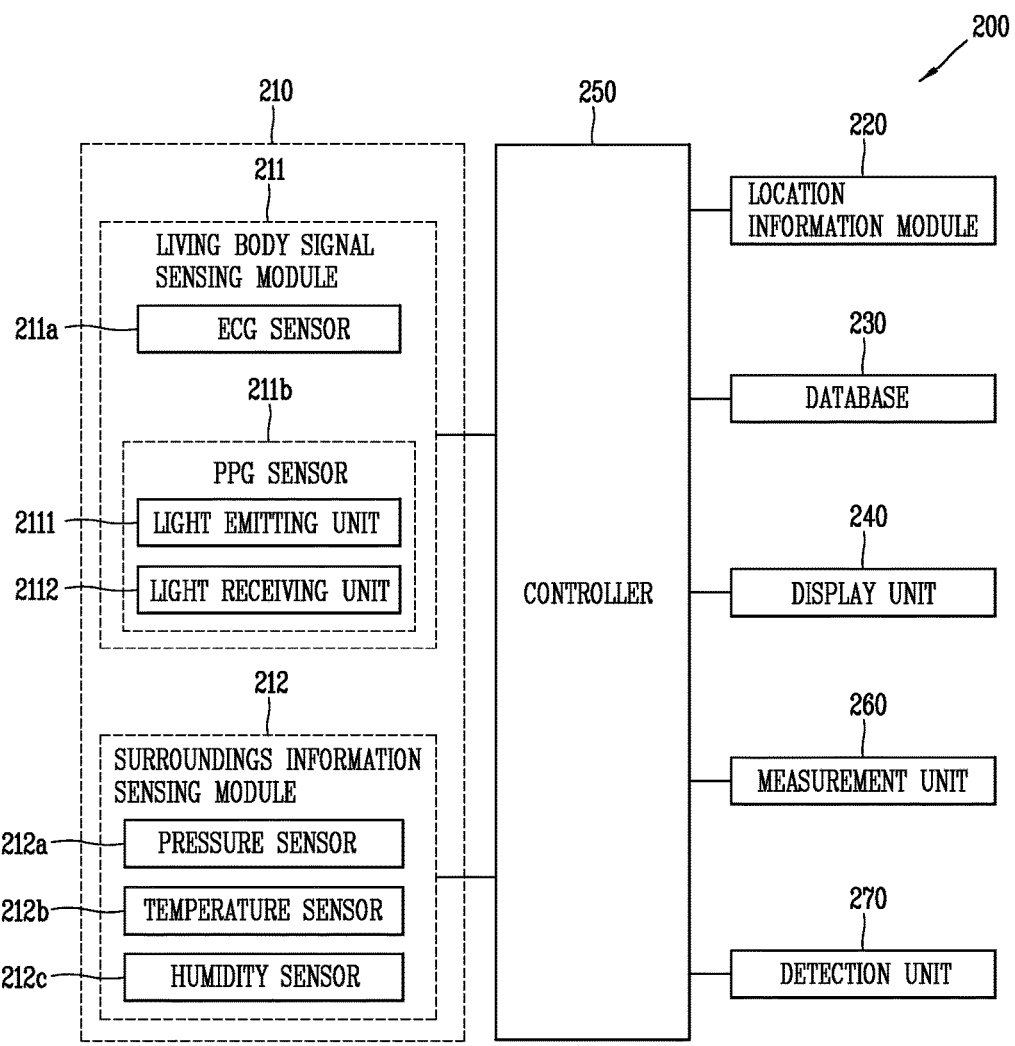
FIG. 3 is a diagram illustrating the mobile terminal according to an embodiment of the present invention.

FIG. 3 is a diagram illustrating a mobile terminal 200 according to an embodiment of the present invention. Referring to FIG. 3, the mobile terminal 200 includes a sensing unit 210, a location information module 220, a database 230, a display unit 240, a measurement unit 260, a detection unit 270 and a controller 250.

The sensing unit 210 includes a living body signal sensing module 211 that senses a living body signal from a user, such as the ECG signal, and the PPG signal when performing the health care function, and a surroundings information sensing module 212 that senses external surroundings information such as pressure (atmospheric pressure) information, temperature (atmospheric temperature) information, and humidity information.

The living body signal sensing module 211 includes an ECG sensor 211a that senses the ECG signal and a PPG sensor 211b that senses the PPG signal.

The ECG sensor 211a senses the ECG signal by measuring the active electric current occurring in the user's heart muscle, via at least two electrodes arranged in the main body of the mobile terminal 200. The PPG sensor 211b includes a light emitting unit 2111 that generates incident light and emits the incident light to an object (for example, a portion of a user's body, such as a finger, and an ear), and a light receiving unit 2112 that receives reflection light reflected in the object. The PPG sensor 211b senses the PPG signal using the reflection light with respect to the incident light. The light emitting unit 2111 may be embodied as a light emitting device (LED) and the light receiving unit 2112 may be embodied as a photodiode (PD).

The surroundings information sensing module 212 includes a pressure sensor 212a that senses the surroundings information such as the external pressure information, the temperature information, and the humidity information, a temperature sensor 212b, and a humidity sensor 212c. However, the surroundings information sensed by the surroundings information sensing module 212 is not limited to what is described above, and may further include various different items of information, such as brightness information and noise information.

The sensing unit 210 may sense the living body signal and the surroundings information by responding to a change in the location of the mobile terminal 200. For example, when the mobile terminal 200 moves from a first area to a second area, the sensing unit 210 may sense the living body signal and the surroundings information that are associated with the location information on the second area. This means that a new living body signal and new surroundings information are automatically collected each time the location of the mobile terminal 200 is changed.

The location information module 220 obtains the location information on the mobile terminal 200. To this end, the location information module 220 receives a global position system (GPS) signal or a cell identification (Cell ID) information. According to the embodiment of the present invention, the location information may be input directly by the user.

The database 230 may be embodied as the memory 160 (refer to FIG. 1) and may store various data relating to the health care function. For example, the database 230 may store a data table for a setting relating to the health care function and a data table for a statistical management of the health care function associated with the location information. As another example, the database 230 may store information on user's personal characteristics, information on a user's health state, and information on a result of medical examination, and the likes. In addition, the memory 160 stores at least one application for managing the health care function.

The display unit 240 displays various screen images relating to the health care function. For example, the display unit 240 displays a screen image resulting from executing the application for managing the health care function. In addition, the display unit 240 may be embodied as a touch screen type that senses a touch input by the user.

The measurement unit 260 may measure a signal to noise ratio (SNR) of the PPG signal. The measurement unit 260 may detect a noise component in the PPG signal sensed by the living body signal sensing module 211 and may compute the signal to noise ratio (SNR) using strength of the PPG signal and strength of the noise component.

The detection unit 270 detects a motion of the main body of the mobile terminal. To this end, the detection unit 270 includes a motion sensor such as a gyro sensor, and an acceleration sensor. In addition, the detection unit 270 provides the controller 250 with motion information that represents the detected degree of motion in terms of a numerical value.

The controller 250 executes an application (hereinafter referred to as a "health care application.") for managing the health care function and controls an overall operation relating to the health care function.

The controller 250 generates numerically-valued living body information, using the living body signal that is sensed by the living body signal sensing module 211 when executing the health care application. For example, the controller 250 generates the numerically-valued living body information, such as the number of heartbeats, heart rate variability (HRV), and oxygen saturation in blood, by analyzing the ECG signal and the PPG signal from the user.

The controller 250 sets a reference range of numerical values that is compared with the living body information, using the surroundings information sensed by the surroundings information sensing module 212. For example, the controller 250 sets the reference range of numerical values for the number of heartbeats or for the oxygen saturation in blood, based on at least one of the external pressure information, the temperature information, and the humidity information. At this point, the controller 250 refers to the data table (refer to FIG. 6A or FIG. 6B) stored in the database 230.

The controller 250 compares the reference range of numerical values with a numerical value of the living body information, and generates alerting information on the user's health state depending on whether or not the numerical value of the living body information falls into the reference range of numerical values.

The reference range of numerical values described above refers to a range of numerical values for the living body signal within which the user's health state is determined as safe in given surroundings. Accordingly, when the numerical value of the living body information is out of the reference range of numerical values, and thus the alerting information is output, the user may be aware that he/she is susceptible to health hazard in the corresponding surroundings.

The controller 250 controls the location information module 220 or the database 230 in such a manner that the database 230 stores the location information obtained by an input by the user, and the living body information, the surroundings information, and the alerting information that are described above in association with one another. In addition, the controller 250 generates map information that represents the expected degree of the hazard relating to the user's health state, using statistical data relating to the information stored in the database 230. Here the statistical data includes an average value of each of the number of heartbeats, the oxygen saturation in blood, the pressure, the temperature, the humidity and the number of alerts. Each of the number of heartbeats, the oxygen saturation in blood, the pressure, the temperature, the humidity and the number of alerts is accumulated in association with the same location information. Generation and display of the map information are described in detail below referring to FIG. 13.

According to the embodiment of the present invention, the expected degree of the hazard to the user that is expressed on the basis of the district (hereinafter referred to as an "expected degree of the hazard") is not limited to the map information and may be realized in various formats. For example, the expected degree of the hazard may be realized in the format of a graph, a data table, a graphic icon, and the likes.

In addition, the controller 250 may compare the signal to noise ratio (SNR) measured by the measurement unit 260 with a pre-set reference value and may control electric current driving the light emitting unit 2111 in such a manner that strength of the incident light being emitted to the object is adjusted depending on the result of the comparison. For example, when the measured signal to noise ratio is smaller than the reference value, the controller 250 may increase an amount of the electric current driving the light emitting unit 2111. Control of the electric current driving the light emitting unit 2111 is described in detail below, referring to FIGS. 8A and 8B, FIGS. 9A and 9B, and FIGS. 10A and 10B.

When the measured signal to noise ratio is equal to or larger than the reference value, the controller 250 generates information on the user's health state by analyzing the PPG signal. For example, the controller 250 obtains heartbeat information such as the user's heart rate variability (HRV) by analyzing the PPG signal, and generates the health state information that represents whether or not the user's health state is good, by using this information. In addition, the controller 250 controls the display unit 240 in such a manner that the display unit 240 displays information on a result of analyzing the PPG signal and the information on the user's health state.

As described above, in the mobile terminal 200 according to the present invention, the strength of the incident light that is emitted to the object to sense the PPG signal may be adjusted based on the signal to noise ratio (SNR) of the PPG signal. As a result, electricity consumption may be decreased. More specifically, the electric current driving the light emitting unit 2111 is controlled in such a manner that in a case where the state of the PPG signal is not comparatively good, the strength of the incident light is increased, and in a case where the state of the PPG signal is comparatively good, the strength of the incident light is maintained or decreased. This means that the electric current driving the light emitting unit 2111 is not always maintained to the maximum value. As a result, the electricity consumption is decreased.

In addition, in the mobile terminal 200 according to the present invention, reliability of the PPG signal may be increased by obtaining the PPG signal using the strength-adjusted incident light before analyzing the PPG signal. For example, an increase in the strength of the incident light may decrease noise in the PPG signal in a situation where the PPG signal is more susceptible to the noise due to is the motion of the mobile terminal 200 or the user's personal characteristics (for example, the skin thickness on which the incident light is incident).

Figure 4:
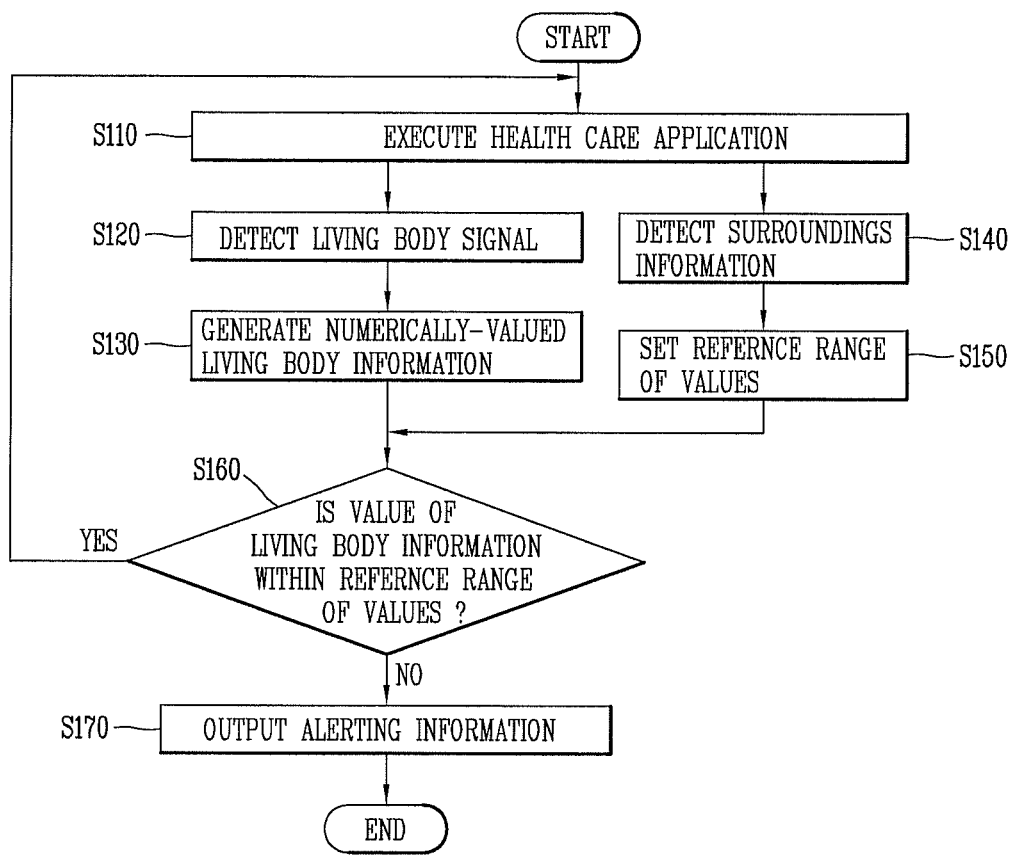
FIG. 4 is a flow chart for describing a method of controlling the mobile terminal according to an embodiment of the present invention.

FIG. 4 is a flow chart for describing a method of controlling a mobile terminal 200 according to an embodiment of the present invention. Referring to FIG. 4, first, Step S110 is performed in which a health care application is executed. When executing the health care application, Step S120 is performed in which a living body signal from a user (for example, an ECG signal, a PPG signal and the like) is sensed. Next, Step S130 is performed in which numerically-valued living body information (for example, the number of heartbeats, the oxygen saturation in blood, and the like) is generated using the living body signal.

In addition, when executing the health care application, Step S140 is performed in which external surroundings information (for example, pressure information, temperature information, humidity information and the like) is sensed. Next, Step S150 is performed in which a reference range of numerical values that is compared with a numerical value of living body information is set using the surroundings information. This means that the reference range of numerical values is variably set depending on the surroundings information.

Subsequently, Step S160 is performed in which it is determined whether or not the numerical value of the living body information falls into the reference range of numerical values. Step S170 is performed in which alerting information on a user's health state is generated and is output in a case where the numerical value of the living body information is out of the reference range of numerical values as a result of the determination.

As described above, in the mobile terminal 200 of the present invention, the variable setting of the reference range of numerical values for the living body information depending on the information on the user's surroundings may make a report on the health state adaptable to the user's surroundings.

Figure 5:
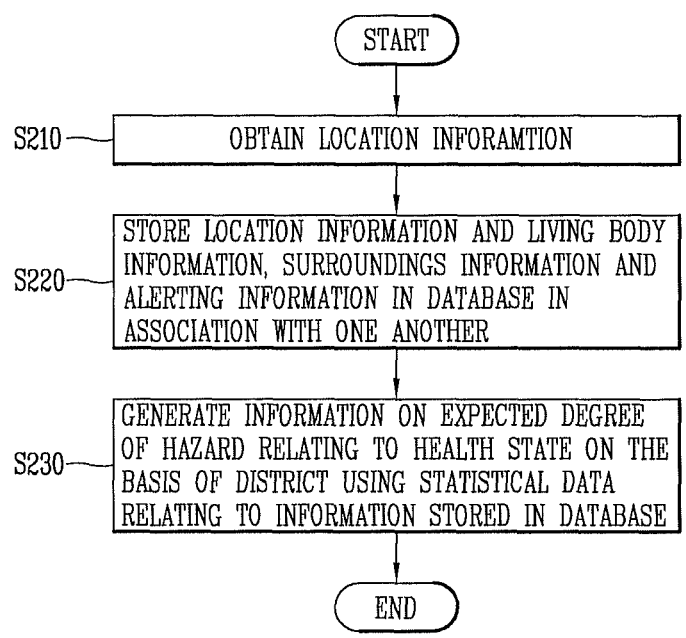
FIG. 5 is a flow chart for describing a method of controlling the mobile terminal according to another embodiment of the present invention.

FIG. 5 is a flow chart for describing a method of controlling a mobile terminal 200 according to another embodiment of the present invention. Referring to FIG. 5, first, when executing a health care application, Step S210 is performed in which information on location of the mobile terminal 200 is obtained. Next, Step S220 is performed in which the location information, and living body information, surroundings information, and alerting information are stored in a database 230 (refer to FIG. 3) in association with one another.

Subsequently, Step S230 is performed in which map information that represents an expected degree of a hazard on the basis of a district using statistical data relating to the information stored in the database 230 is generated.

As described above, in the mobile terminal 200 according to the present invention, information relating to a health care function, collected from many districts, may be accumulatively stored in the database 230, and thus the map information representing the expected degree of the hazard on the basis of the district using the statistical data relating to the information stored in the database 230 may be provided to enable the user to easily be aware of the expected degree of the hazard prior to a user's visit to a given district.

FIGS. 6A and 6B are views, each illustrating a data table stored in the database 230 according to the embodiment of the present invention. The data table in FIG. 6A provides a reference range of numerical values for the number of heartbeats, which corresponds to each of pressure information, temperature information and humidity information. The data table in FIG. 6B provides a reference range of numerical values for oxygen saturation in blood, which corresponds to each of the pressure information, the temperature information and the humidity information. Accordingly, the reference range of numerical values for the living body information, which corresponds to the current surroundings information, may be set using these data tables.

Figure 7:
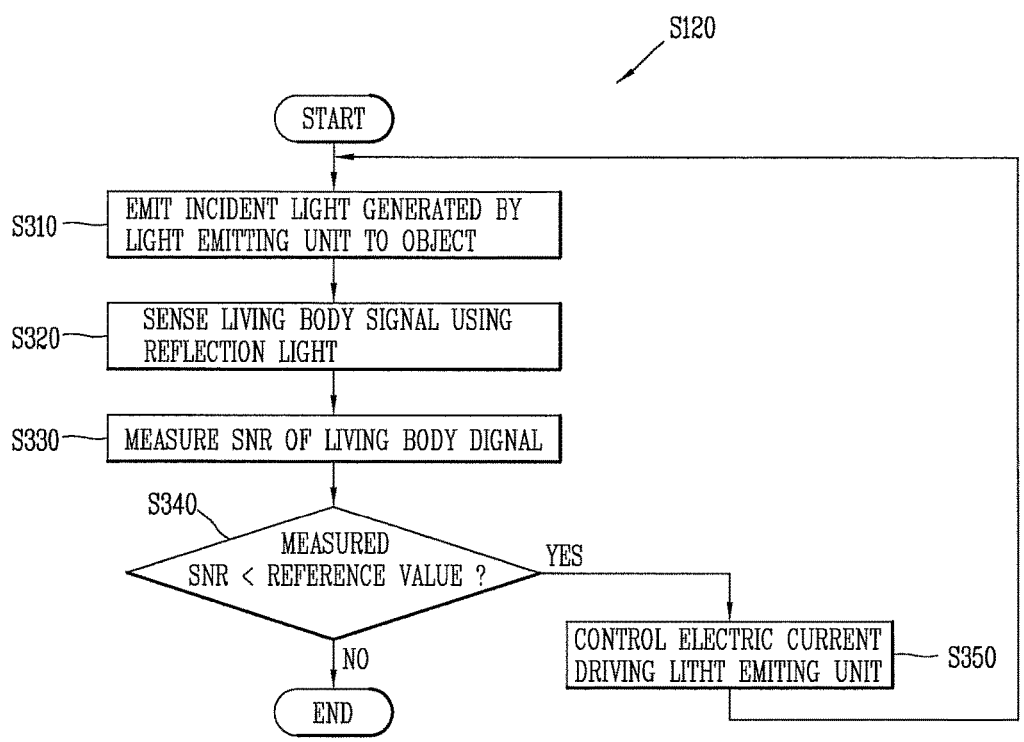
FIG. 7 is a flow chart for describing the method of controlling the mobile terminal according to the embodiment of the present invention.

FIG. 7 is a flow chart for describing the method of controlling the mobile terminal 200 according to the embodiment of the present invention. Specifically, FIG. 7 is a flow chart for describing in detail Step S120 (refer to FIG. 4) of sensing a living body signal.

Referring to FIG. 7, first, Step S310 is performed in which incident light generated by a light emitting unit 2111 (refer to FIG. 3) is emitted to an object. Next, Step S320 is performed in which reflection light is received from the object and the living body signal, for example, a PPG signal is sensed using the reflection light.

Subsequently, Step S330 is performed in which a signal to noise ratio (SNR) of the PPG signal is measured and Step 340 is performed in which a pre-set reference value is compared with the measured signal to noise ratio (SNR). Next, Step S350 is performed in which electric current driving a light emitting unit 2111 is controlled in such a manner that strength of the incident light incident on the object is adjusted depending on the result of comparing the reference value with the measured signal to noise ratio (SNR). For example, when the signal to noise ratio (SNR) is smaller than the reference value, an amount of the electric current driving the light emitting unit 2111 is increased. The electric current driving the light emitting unit 2111 may be automatically controlled, based on the data table, and the electric current driving the light emitting unit 2111 may be manually controlled based on an input by the user.

In this manner, when the amount of the electric current driving the light emitting unit 2111 is increased, the strength of the incident light and the strength of the reflection light are increased. As a result, strength of the PPG signal is increased, compared to the noise component, and thus the signal to noise ratio of the PPG signal is decreased. This means that the reliable PPG signal is obtained.

On the other hand, when the signal to noise ratio (SNR) that is measured is equal to or less than the reference value, this is, when it is determined that the reliable PPG signal is obtained, Step S130 (refer to FIG. 4) starts in which numerically-valued living body information is generated by analyzing the PPG signal.

According to the embodiment of the present invention, in Step S310 of emitting the incident light to the object, or in Step S350 of controlling the electric current driving the light emitting unit 2111, an amount of the electric current driving the light emitting unit 2111, or an increased amount of the electric current driving the light emitting unit 2111 may be determined depending on various references. A description of this is provided in detail below.

Figures 8A, 8B:
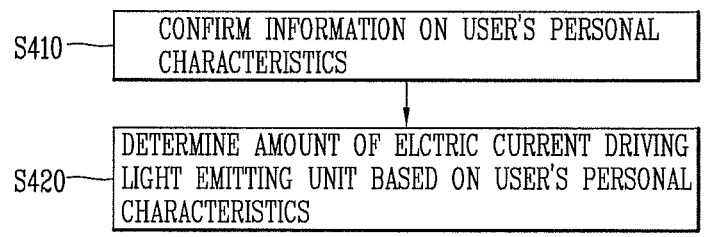
FIG. 8A is a flow chart for describing an embodiment of a method of controlling electric current driving a light emitting unit.
FIG. 8B is a view illustrating the data table that is referred to in the method of controlling the electric current in FIG. 8A.

FIG. 8A is a flow chart for describing an embodiment of a method of controlling electric current driving the light emitting unit 2111. FIG. 8B is a view illustrating a data table that is referred to in the method of controlling the electric current in FIG. 8A.

Referring to FIGS. 8A and 8B, the method of controlling drive electric current according to the embodiment includes Step S410 of confirming information on user's personal characteristics and Step S420 of determining an amount of the electric current driving the light emitting unit 2111 and the increased amount electric current driving the light emitting unit 2111, based on the information on the user's personal characteristics.

Here, the information on the user's personal characteristics includes, for example, items of information on age, stature weight, skin thickness, and the like. In particular, the skin thickness is used as a factor associated closely with control of the electric current driving the light emitting unit 2111. For example, as illustrated in FIG. 8B, the control is performed in such a manner that as the skin thickness is more increased, the amount of the electric current driving the light emitting unit 2111 is more increased.

According to the embodiment of the present invention, the light emitting unit 2111 may be initially driven by the amount of the electric current that is determined, based on the information on the user's personal characteristics. That is, the amount of the electric current driving the light emitting unit 2111 may be determined in advance, based on the information on the user's personal characteristics, in Step S310 (refer to FIG. 7) of initially emitting the incident light generated by the light emitting unit 2111 to the object.

In addition, the amount of the electric current driving the light emitting unit 2111 is determined based the information on the user's personal characteristics, in Step S350 (refer to FIG. 7) of controlling the electric current driving the light emitting unit 2111 depending on a result of comparing the signal to noise ratio (SNR) with the reference value while the incident light is emitted to the object. For example, in a case where the amount of the electric current corresponding to the user's skin thickness is greater than a current amount of the electric current, the amount of the electric current driving the light emitting unit 2111 is increased in such a manner that the amount of the electric current corresponding to the thickness of the user's skin drives the light emitting unit 2111. At this point, the increased amount of the electric current driving the light emitting unit 2111 is a difference between the amount of the electric current corresponding to the thickness of the user's skin and the current amount of the electric current.

Figures 9A, 9B:
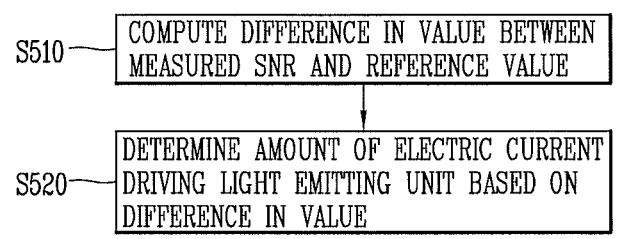
FIG. 9A is a flow chart for describing an embodiment of a method of controlling electric current driving a light emitting unit.
FIG. 9B is a view illustrating the data table that is referred to in the method of controlling the electric current in FIG. 9A.

Referring to FIGS. 9A and 9B, the method of controlling drive electric current according to the embodiment includes Step S510 of computing a difference in value between the signal to noise ratio (SNR) of the PPG signal and the reference value (hereinafter referred to as a "difference value.") and Step S520 of determining the amount of the electric current driving the light emitting unit 2111 or the increased amount of the electric current driving the light emitting unit 2111.

According to the embodiment of the present invention, while the incident light is emitted to the object, the increased amount of the electric current driving the light emitting unit 2111 is determined, based on the difference value, in Step S350 (refer to FIG. 7) of controlling the electric current driving the light emitting unit 2111 depending on the result of comparing the signal to noise ratio of the PPG signal with the reference result. For example, as illustrated in FIG. 9B, the control is performed in such a manner that as the signal to noise ratio (SNR) of the PPG signal is smaller than the reference value, the amount of the electric current driving the light emitting unit 2111 is more increased.

FIG. 10A is a flow chart for describing the embodiment of the method of controlling electric current driving the light emitting unit 2111. FIG. 10B is a view illustrating the data table referred to in the control method of controlling the electric current driving the light emitting unit 2111 as illustrated FIG. 10A.

Referring to FIGS. 10A and 10B, the method of controlling the drive electric current according to the embodiment includes Step S610 of sensing a motion of the main body of the mobile terminal, and Step S620 of determining the amount of the electric current driving the light emitting unit 2111 or the increased amount of the electric current driving the light emitting unit 2111, based on the motion of the main body of the mobile terminal.

According to the embodiment of the present invention, while the incident light is emitted to the object, the amount of the electric current driving the light emitting unit 2111 may be determined, based on the motion of the main body of the mobile terminal, in Step S350 (refer to FIG. 7) of controlling the electric current driving the light emitting unit 2111 depending on the result of comparing the signal to noise ratio of the PPG signal with the reference result. For example, in a case where the amount of the electric current corresponding to the degree of the motion of the main body of the mobile terminal is greater than the current amount of the electric current, the amount of the electric current driving the light emitting unit 2111 may be increased in such a manner that the light emitting unit 2111 is driven by the amount of the electric current corresponding to the degree of the motion of the main body of the mobile terminal. At this point, the increased amount of the electric current driving the light emitting unit 2111 is a difference between the degree of the motion of the main body of the mobile terminal and the current amount of the electric current.

The mobile terminal 200 according to the embodiment of the present invention is equipped with an application (hereinafter referred to a "health care application.") for managing the health care function as described above. The user interface is described below, which is provided by the health care application.

Figure 11:
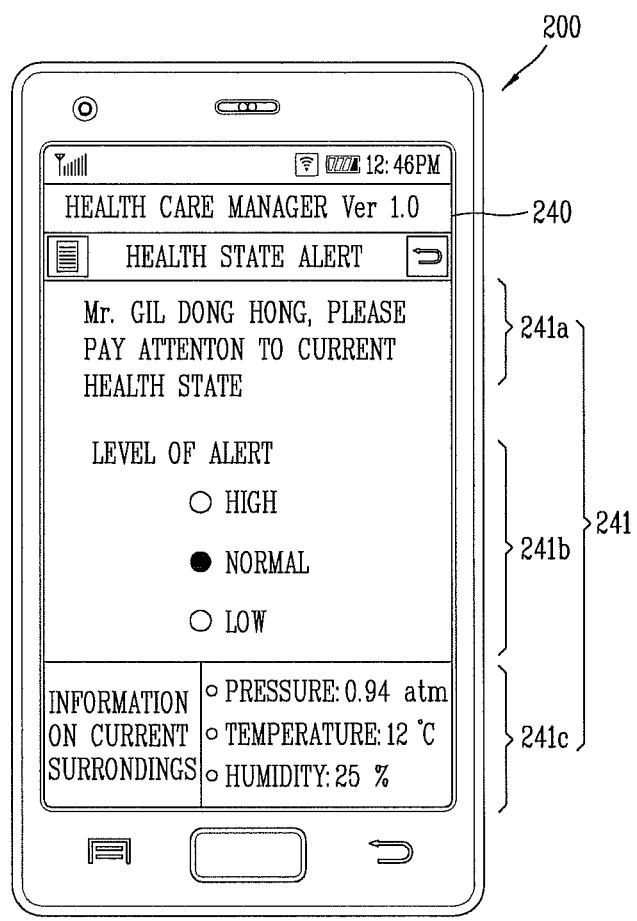
FIGS. 11 to 13 are views, each illustrating a user interface of the mobile terminal according to the embodiment of the present invention.
Figure 12:
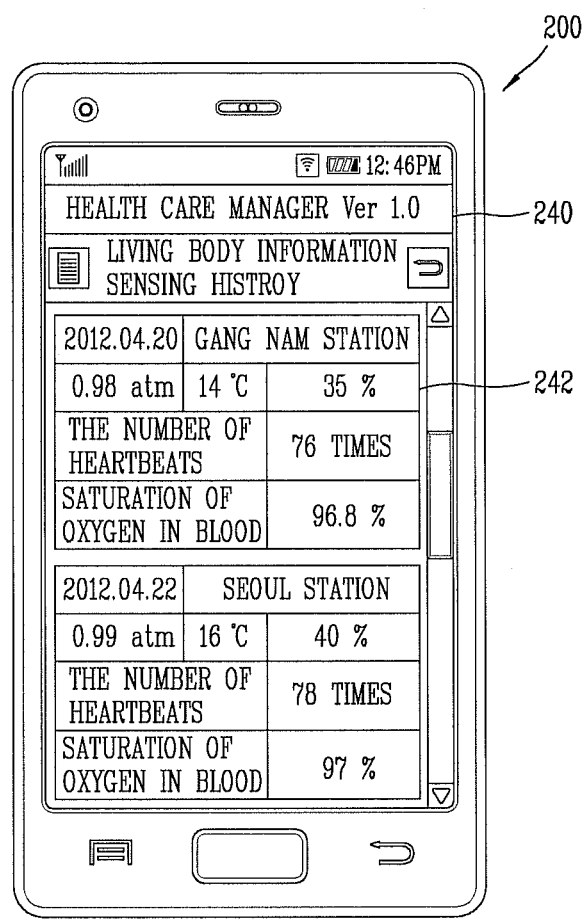
Figure 13:
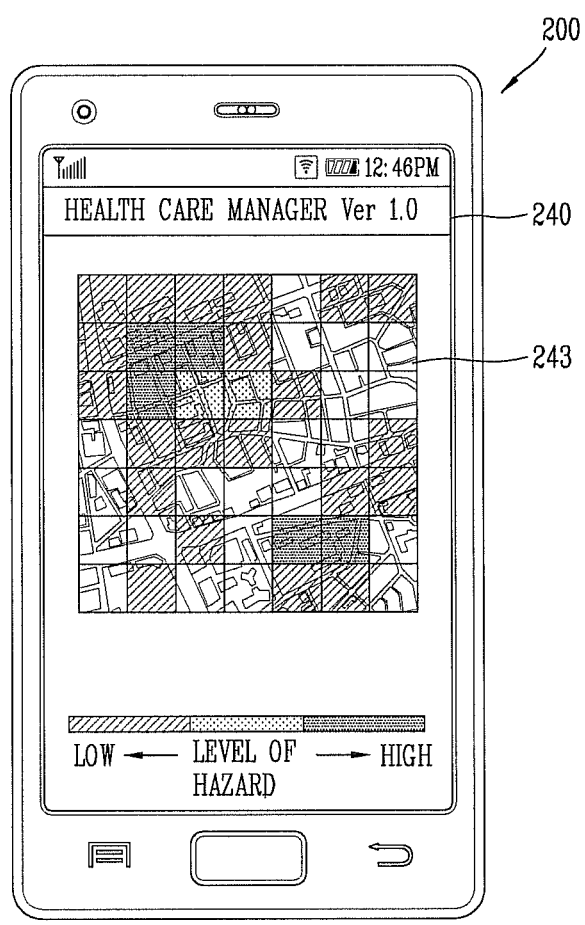

FIGS. 11 to 13 are views, each illustrating the user interface of the mobile terminal 200 according to the embodiment of the present invention. Descriptions of the user interface which overlap with the descriptions of the health care function provided above are omitted below.

Referring to FIG. 11, the controller 250 (refer to FIG. 3) may control the display unit 240 in such a manner that the alerting information 241 on the user's health state is displayed on the screen image resulting from executing the health care application in a case where the numerical value of the living body information is out of the reference range of numerical values. As illustrated in the drawings, the alerting information 241 includes an alerting message 241a, an alerting level 241b, and current information 241c on the user's surroundings.

In addition, the controller 250 may determine the alerting level 241b, based on the degree to which the numerical value of the living body signal is out of the reference range of numerical values. For example, in a case where the degree to which the numerical value of the number of heartbeats is out of the reference range of numerical values is 1 to 5 (times per one minute), the alerting level may be determined as "LOW." In a case where the degree to which the numerical value of the number of heartbeats is out of the reference range of numerical values is 6 to 10 (times per one minute), the alerting level may be determined as "NORMAL." In a case where the degree to which the numerical value of the number of heartbeats is out of the reference range of numerical values is 11 or more (times per one minute), the alerting level may be determined as "HIGH."

In addition, the controller 250 may control the display unit 240 in such a manner that the alerting level 241b is displayed in the form of a graphical icon. For example, the alerting level 241b may be realized as the graphical icon such as a signal lamp, in such a manner that a "HIGH" level, a "NORMAL" level, and a "HIGH" level correspond to "RED," "YELLOW," and "GREEN," respectively. Accordingly, the user is able to be intuitively aware of the degree of his/her health state.

Referring to FIG. 12, the controller 250 controls the display unit 240 in such a manner that detection history information 242 with regard to the information on user's living body is displayed on the screen image resulting from executing the health care application. As illustrated in the drawings, the detection history information 242 is realized as the data table that includes the time information, the location information, the pressure information, the temperature information, the humidity information, the number of heartbeats, the oxygen saturation in blood, and the like at the time of generating the living body information. In addition, the detection history information 242 is accumulatively stored in the database 230 and is managed each time the living body information is generated. Accordingly, the user is able to refer to the details of his/her health state at a past specific situation.

Referring to FIG. 13, the controller 250 controls the display unit 240 in such a manner that map information 243 showing the expected degree of the hazard on the basis of the district is displayed on the screen image resulting from executing the health care application.

As described above, the map information 243 is generated based on the statistical data relating to the information stored in the database 230. More specifically, the map information 243 includes information on the districts, and the expected degree of the hazard for each district is determined based on at least one of the averaged number of the heartbeats, the averaged oxygen saturation in blood, the averaged pressure, the averaged temperature, the averaged humidity, and the averaged number of the alerts. Each of the number of the heartbeats, the oxygen saturation in blood, the pressure, the temperature, the humidity, and the number of the alerts is accumulated in association with the location information corresponding to each district.

In addition, graphical information is defined which represents each level of the expected degree of the hazard to distinguish among the levels of the expected degree of the hazard. For example, the district that is at the high level of the expected degree of the hazard and the district that is at the low level of the expected degree of the hazard may be assigned different colors, or different brightness levels, respectively.

In addition, the district that the user has visited and the district he/she has not visited may be distinguished from each other to be displayed in the map information 243. For example, the expected degree of the hazard may not be displayed with respect to the district on which the statistical data is not able to be detected, that is, with respect to the district that the user has not visited.

The controller 250 may update the map information 243 when a change occurs in at least part of the statistical data. More specifically, the controller 250 newly generates the map information 243 that reflects the change in the estimated degree of the hazard, in a case where the change occurs in at least part of the statistical data and thus results in a change in the expected degree of the hazard because the living body information (the living body signal), the surroundings information, and the like are newly collected when the location of the mobile terminal 200 is changed.

Figure 14:
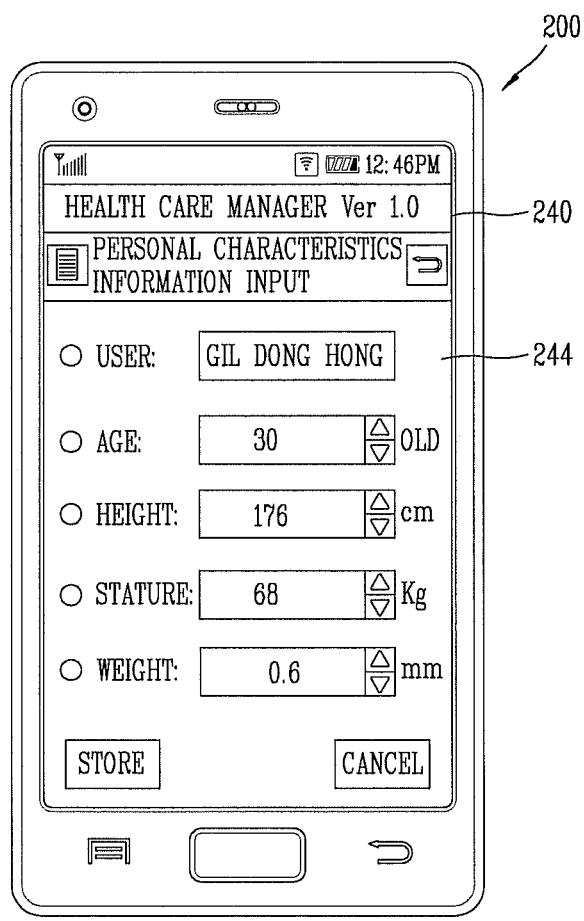
FIG. 14 is a conceptional view illustrating the user interface of the mobile terminal relating to an input of information on personal characteristics according to the embodiment of the present invention.

FIG. 14 is a conceptual view illustrating the user interface of the mobile terminal 200 relating to an input of the information on the personal characteristics according to the embodiment of the present invention. Referring to FIG. 14, the controller 250 (refer to FIG. 3) controls the display unit 240 in such a manner that a menu screen image 244 is displayed for inputting the information on the user's personal characteristics when executing the health care application.

The user inputs the information on the personal characteristics information through the use of the menu screen image 244, such as the user's name, age, stature, weight, and skin thickness. However, the information on the personal characteristics that is able to be input is not limited to what is illustrated, and may be changed in a various manner. The information on the personal characteristics that is input by the user is organized into the database, and the database-organized information is stored in the memory 160 (refer to FIG. 1).

Figure 15:
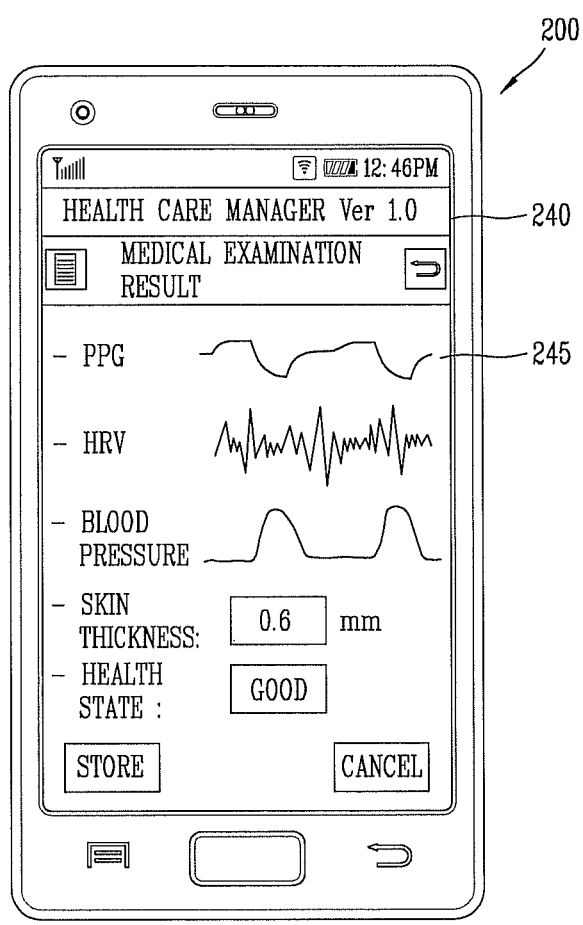
FIG. 15 is a conceptional view illustrating the user interface of the mobile terminal relating to the result of medical examination according to the embodiment of the present invention.

FIG. 15 is a conceptual view illustrating the user interface of the mobile terminal 200 relating to the result of the medical examination according to the embodiment of the present invention. Referring to FIG. 15, the controller 250 controls the display unit 240 in such a manner that the display unit 240 displays a screen image 245 including the health state information, the information on the skin thickness, and the like that result from analyzing the PPG signal. The result of analyzing the PPG signal, and the health state information are realized as the form of a graphic, a table, a text, and the like. The result of analyzing the PPG signal, and the health state information are organized into the database and the database-organized information is stored in the memory 160.

Figure 16A:
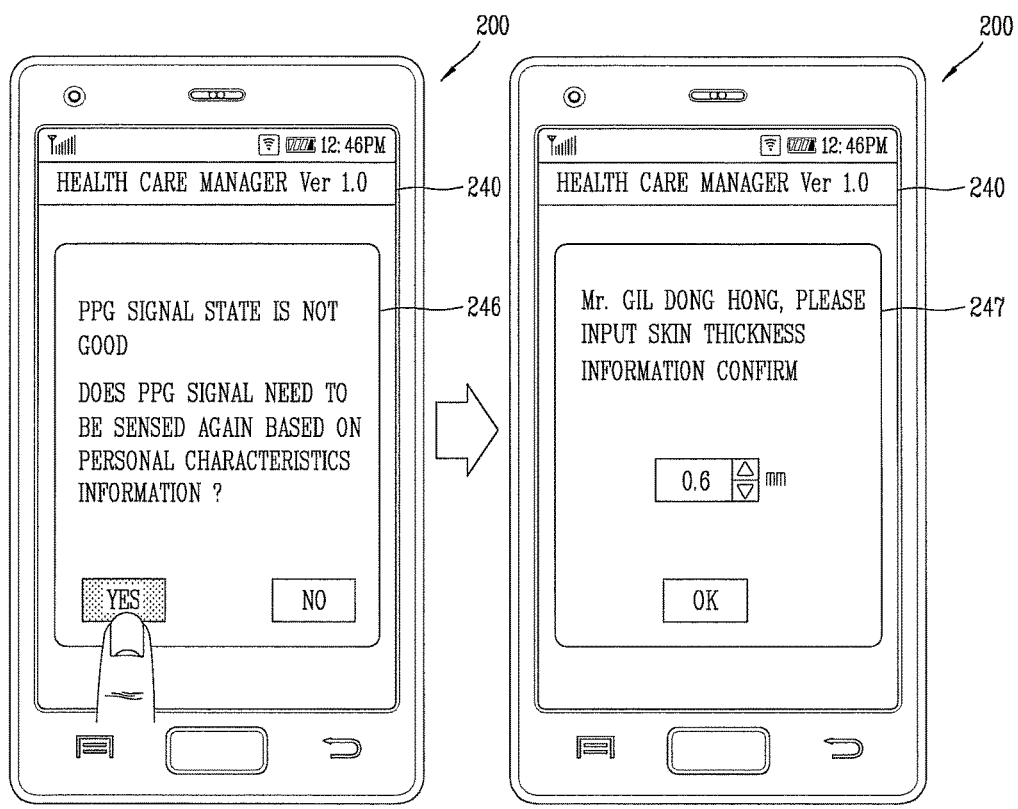
FIGS. 16A and 16B are conceptional views, each illustrating the user interface of the mobile terminal relating to the control of the electric current driving the light emitting unit according to the embodiment of the present invention.
Figure 16B:
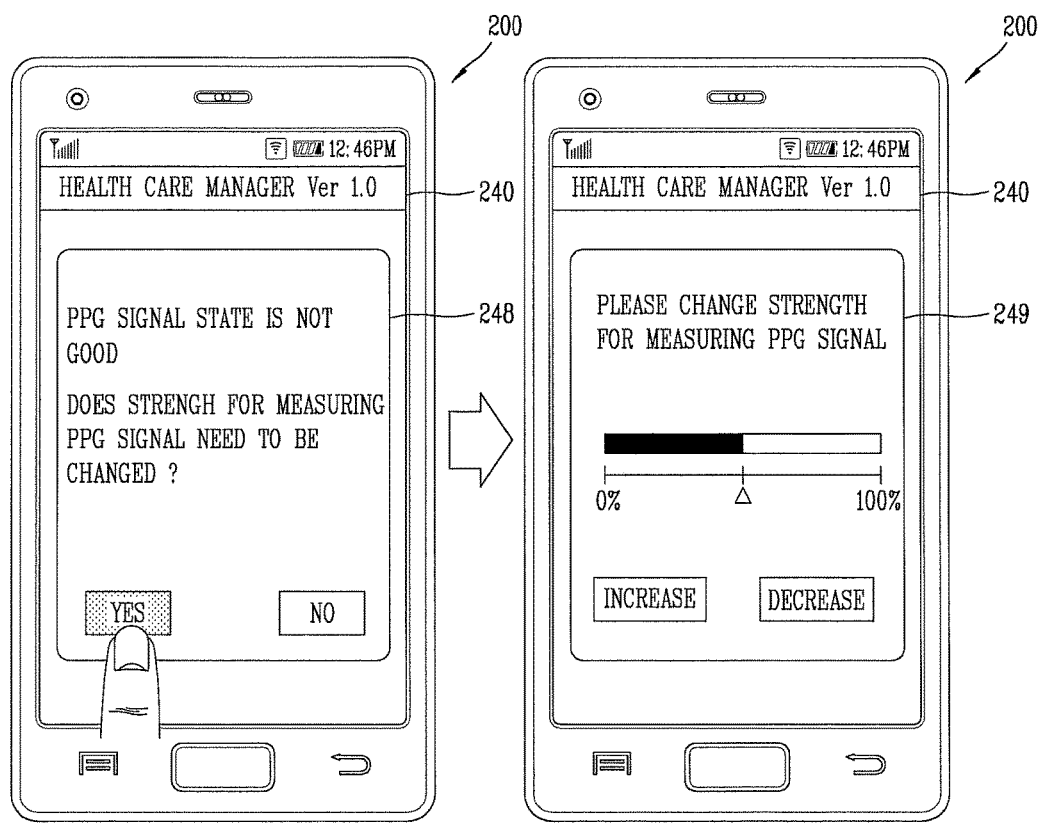

FIGS. 16A and 16B are conceptual views, each illustrating the user interface of the mobile terminal 200 relating to the control of the electric current driving the light emitting unit 2111 according to the embodiment of the present invention.

Referring to FIG. 16A, when the PPG signal sensed by the living body signal sensing module 211 (refer to FIG. 3) is determined as decreasing in reliability, that is, in a case where the signal to noise ratio of the PPG signal is smaller than the reference value, the controller 250 controls the display unit 240 in such a manner that the display unit 240 displays a menu screen image 263 relating to the sensing of the PPG signal. At this point, a menu screen image 246 includes a menu button and the like for selecting whether the PPG signal is again sensed based on the message indicating that the state of the PPG signal is not good and the information on the user's personal characteristics. In addition, the menu screen image 246 may be realized as a pop-up window.

In a case where the user inputs a command to again sense the PPG through the use of the menu button on the menu screen image 246, the controller 250 increases the amount of the electric current driving the light emitting unit 2111 in such a manner that the strength of the incident light being emitted to the object is increased based on the information on the user's personal characteristics stored in the memory 160. Then, the controller 250 controls the living body signal sensing module 211 in such a manner that the living body signal sensing module 211 again senses the PPG signal. At this point, since the again-sensed PPG signal results from the incident light having the increased strength, the reliability of the PPG signal is improved.

In addition, in a case where the user inputs the command to again sense the PPG signal through the use of the menu button on the menu screen image 246, the controller 250 controls the display unit 240 in such a manner that the display unit 240 displays a menu screen image 247 for inputting the information on the user's personal characteristics, for example, the information on the skin thickness, as illustrated in the drawings. In a case whether the user inputs the information on the skin thickness through the use of the menu screen image 247, the controller 250 increases the amount of the electric current driving the light emitting unit 2111 in such a manner that the strength of the incident light being emitted to the object is increased based on the information on the skin thickness that is newly input.

Referring to FIG. 16B, in the same manner as illustrated in FIG. 16A, in a case where the signal to noise ratio of the PPG signal sensed by the living body signal sensing module 211 is smaller than the reference value, the controller 250 controls the display unit 240 in such a manner that the display unit 240 displays a menu screen image 248 relating to the sensing of the PPG signal. At this point, the menu screen image 248 includes the menu button and the like for selecting whether to change the message indicating that the PPG signal is not good, and the strength to sense the PPG signal. The change in the strength to sense the PPG signal means a change in the amount of the electric current driving the light emitting unit 2111.

In a case where the user inputs a command to change the strength to sense the PPG signal through the use of the menu button on the menu screen image 248, the controller 250 controls the display unit 240 in such a manner that the display unit 240 displays a menu screen image 249 for selecting an increase or a decrease in the strength to sense the PPG signal. In a case where the user selects the increase or decrease in the strength to sense the PPG signal through the use of the menu screen image 249, the controller 250 controls the amount of the electric current driving the light emitting unit 2111 to increase or decrease the strength of the incident light being emitted to the object.

Figure 17A:
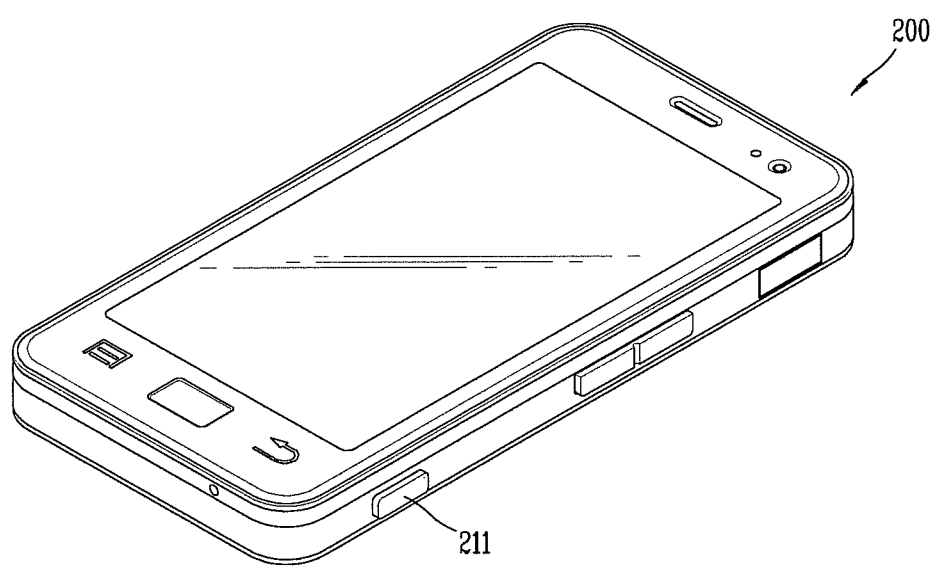
FIG. 17A is a conceptional view illustrating an example in which a living body signal sensing module according to the present invention is provided in the mobile terminal.
Figure 17B:
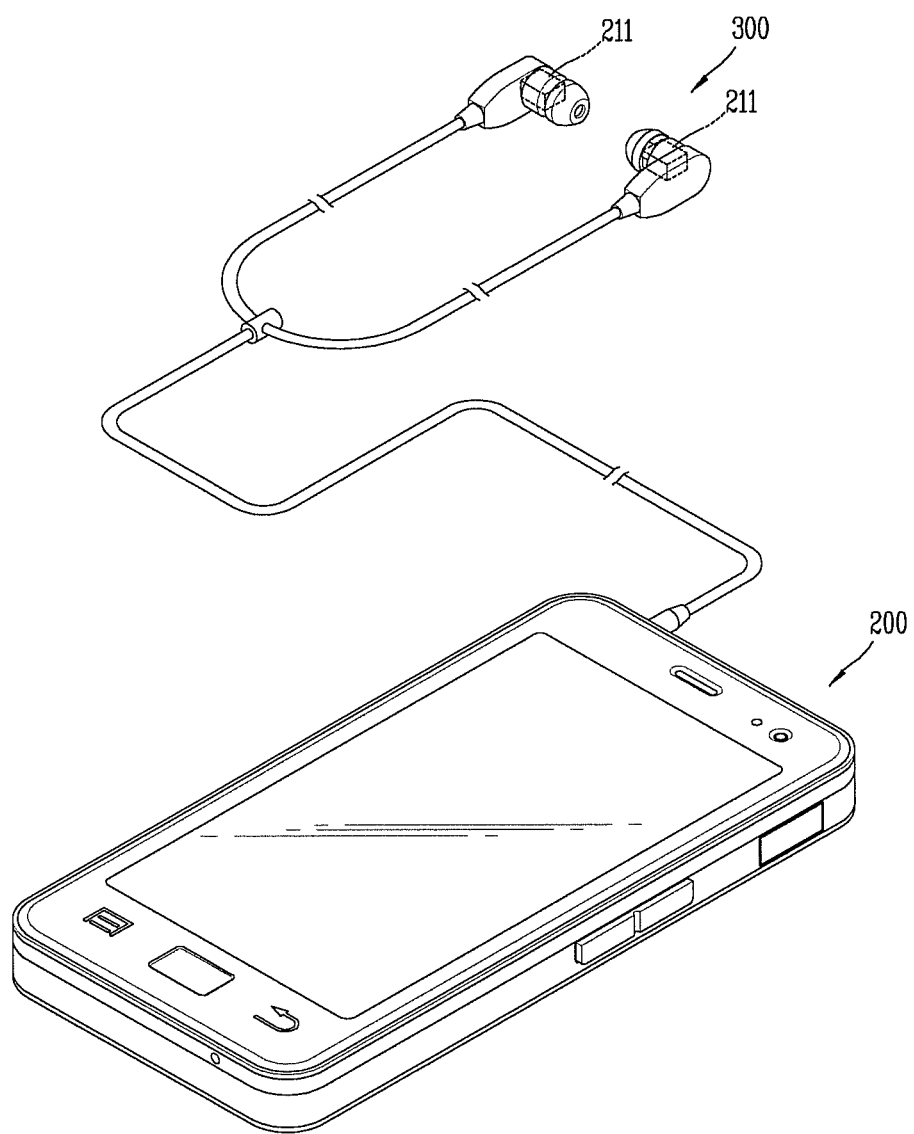
FIG. 17B is a conceptional view illustrating an example in which the living body signal sensing module according to the present invention is provided in an accessory device.

FIG. 17A is a conceptual view illustrating an example in which the living body signal sensing module 211 according to the present invention is provided in the mobile terminal 200. FIG. 17B is a conceptual view illustrating an example in which the living body signal sensing module 211 according to the present invention is provided in an accessory device 300.

Referring to FIG. 17A, the living body signal sensing module 211 is positioned in a portion of the main body of the mobile terminal. More specifically, the living body signal sensing module 211 is positioned in the portion that is able to naturally come into contact with the user's skin in a state where the user holds the mobile terminal 200 with his/her hand.

Referring to FIG. 17B, a constituent element making up the living body signal sensing module 211 may be positioned in the accessory device 300 that connects to the mobile terminal 200. Here the accessory device 300 refers to a device that is designed in such a manner as to connect to a portion of the user's body, such as an earphone, and a finger-clipped sensor. In addition, the accessory device 300 may connect to the mobile terminal 200 in a wireless or wire manner for communication between them.

According to the embodiment disclosed in the present disclosure, the method described above may be realized by being stored as processor-readable codes in a program-stored media. A ROM, a RAM, a CD-ROM, a magnetic tape, a floppy disk, an optical data storage device and the like are an example of the processor-readable media, and the processor-readable media may be realized in the form of a carrier wave (for example, a transmission over the Internet).

The configuration and the method relating to the mobile terminal described in the present disclosure according to the embodiment are not applied in a limiting manner, but all of or some of the embodiments may be selectively combined with each other to create various modifications to the embodiments.

In the mobile terminal according to the present invention, the variable setting of the reference range of numerical values for the living body information depending on the information on the user's surroundings may make a report on the health state adaptable to the user's surroundings in determining the user's health state.

The information relating to the health care function, collected from many districts is accumulatively stored and the map information showing the expected degree of the hazard on the basis of a district is provided using the statistical data relating to the information stored in the database. As a result, the user may be aware of the expected degree of the hazard easily and in advance before visiting a specific district.

In the mobile terminal according to the present invention, the strength of the incident light that is emitted to the object in order to sense the PPG signal may be adjusted based on the signal to noise ratio of the PPG signal (the living body signal), thereby decreasing power consumption.

In addition, in the mobile terminal according to the present invention, the obtaining of the PPG signal using the strength-adjusted incident light before analyzing the PPG signal increases the reliability of the PPG signal.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. A mobile terminal with a health care function, comprising:
   a display;
   a sensing unit that includes a living body sensor that is configured to sense a living body signal from a user and a surroundings information sensor that is configured to sense information on user's surroundings when performing the health care function, wherein the living body sensor includes a "electrocardiogram (ECG) sensor" and a photoplethysmography (PPG) sensor and the surroundings information sensor includes a pressure sensor generating external pressure information, temperature sensor generating temperature information, and humidity sensor generating humidity information;
   a controller is configured to:
      generate a numerically-valued living body information using the living body signal, set a reference range of numerical values using the information on the user's surroundings, wherein the reference range of numerical values includes a minimum (MIN) value and a maximum (MAX) value;
      change at least one of the MIN value and the MAX value based on the external pressure information, the temperature information, and the humidity information,
      generate alerting information depending on whether or not a numerical value of the living body information falls into the changed reference range of numerical values; and
      display, via the display, the alerting information,
   wherein the living body sensor includes:
      a light emit diode (LED) that emits incident light to the user; and
      a photo diode (PD) that receives reflection light reflected in the user,
   wherein, the controller is further configured to:
      measure a signal to noise ratio (SNR) of the living body signal using the reflection light;
      determine whether or not the signal to noise ratio is less than a reference value;
      display, via the display, a menu screen image for selecting an increase or a decrease in strength of the incident light when the signal to noise ratio is determined to be less than the reference value; and
      control an amount of electric current that drives the light emit diode to increase or decrease the strength of the incident light in response to a user input at the displayed menu screen image.

2. The mobile terminal with a health care function, according to claim 1, further comprising:
   global position system (GPS) configured to sense information on location of the mobile terminal; and
   a database that stores the location information and the living body information, the surroundings information, and the alerting information in association with one another.

3. The mobile terminal with a health care function, according to claim 2,
   wherein the controller generates map information representing an expected degree of a hazard on the basis of a district using statistical data relating to the information stored in the database.

4. The mobile terminal with a health care function, according to claim 3,
   wherein the controller updates the map information when a change occurs in at least part of the statistical data.

5. The mobile terminal with a health care function, according to claim 1, further comprising:
   a detection unit including a gyro sensor and an acceleration sensor, and the detection unit is configured to detect a motion of a main body of the mobile terminal,
   wherein the controller determines the amount of the electric current that drives the light emit diode, based on the motion of the main body of the mobile terminal.

6. The mobile terminal with a health care function, according to claim 1, wherein a constituent element making up the living body sensor is positioned in a main body of the mobile terminal or an accessory device that connects to the main body of the mobile terminal.

7. The mobile terminal with a health care function, according to claim 1,
wherein the controller determines an alerting level of the alerting information, based on the degree to which the numerical value of the living body signal is out of the reference range of the numerical values.

8. The mobile terminal with a health care function, according to claim 1,
wherein the sensing unit responds to a change in location of the mobile terminal to sense the living body signal and the surroundings information.

9. The mobile terminal with a health care function, according to claim 1,
wherein the living body signal includes at least one of an electrocardiogram (ECG) signal, and a photoplethysmography (PPG) signal.

10. The mobile terminal with a health care function, according to claim 1,
wherein the living body information includes at least one of a number of heartbeats and oxygen saturation in blood.

11. The mobile terminal with a health care function, according to claim 1, further comprising:
an accessory device including at least one earphone and finger-clipped sensor and configured to connect to the mobile terminal in a wireless or wire manner for communication, wherein the accessory device includes a first and a second output modules configured to output audio signals,
wherein the living body sensor includes a first ECG sensor disposed at the first output module, and a second ECG sensor disposed at the second output module, wherein the first and second ECG sensors sense an ECG signal by measuring an active electric current occurring in a user's heart muscle.

12. A method of controlling a mobile terminal with a health care function, comprising:
sensing, via an ECG sensor and a PPG sensor of the mobile terminal, a living body signal from a user when performing the health care function;
sensing, via a pressure sensor, a temperature sensor and a humidity sensor of the mobile terminal, information on user's surroundings information when performing the health care function, wherein the information includes external pressure information, temperature information, and humidity information;
generating, via a controller of the mobile terminal, a numerically-valued living body information using the living body signal;
setting, via the controller, a reference range of numerical values using the information on the user's surroundings, wherein the reference range of numerical values includes a minimum (MIN) value and a maximum (MAX) value;
changing, via the controller, at least one of the MIN value and the MAX value based on the external pressure information, the temperature information, and the humidity information; and
generating, via the controller, alerting information depending on whether or not a numerical value of the living body information falls into the reference range of numerical values, wherein the alerting information is generated based on the changed at least one of the MIN value and the MAX value;
displaying, via the controller, the alerting information on a display of the mobile terminal,
wherein the sensing of the living body signal from the user includes:
emitting incident light generated by a light emit diode to the user, and
sensing the living body signal from the user, by using the reflection light reflected in the user, and
wherein the method further comprises:
measuring a signal to noise ratio (SNR) of the living body signal using the reflection light;
determining whether or not the signal to noise ratio is less than a reference value;
displaying a menu screen image for selecting an increase or a decrease in strength of the incident light to sense the living body signal when the signal to noise ratio is determined to be smaller than the reference value; and
controlling an amount of electric current for driving the light emit diode to increase or decrease the strength of the incident light in response to a user input at the menu screen image.

13. The method of controlling a mobile terminal with a health care function, according to claim 12, further comprising:
obtaining information on location of the mobile terminal; and
storing the location information and the living body information, the surroundings information, and the alerting information in a database, in association with one another.

14. The method of controlling a mobile terminal with a health care function, according to claim 13, further comprising:
generating map information representing an expected degree of a hazard on the basis of a district using statistical data relating to the information stored in the database.

15. The method of controlling a mobile terminal with a health care function, according to claim 14, further comprising:
updating the map information when a change occurs in at least part of the statistical data.

16. The method of controlling a mobile terminal with a health care function, according to claim 12, further comprising:
detecting a motion of a main body of the mobile terminal,
wherein the amount of the electric current for driving the light emit diode is determined based on the motion of the main body of the mobile terminal, in the emitting of the incident light to the object, or in the controlling of the electric current for driving the light emit diode.

17. The method of controlling a mobile terminal with a health care function, according to claim 12,
wherein the living body signal and the surroundings information responds to the change in the location of the mobile terminal, and thus is detected, in the detecting of the living body signal and the surroundings information.

* * * * *